(12) United States Patent
Zook et al.

(10) Patent No.: US 8,118,736 B2
(45) Date of Patent: Feb. 21, 2012

(54) METHOD OF ACCESSING A BLADDER AND ASSOCIATED APPARATUS THEREFOR

(75) Inventors: Ronald E. Zook, Bigfork, MT (US);
Timothy E. Braun, Kalispell, MT (US);
Kenneth A. High, Helena, MT (US);
Laurence K. Sampson, Denver, CO (US); Steve W. Jackinsky, Denver, CO (US); Pete W. Kroehl, Denver, CO (US);
Davey B. Palmer, Highlands, CO (US);
David W. Wright, Littleton, CO (US);
Paul P. Burek, Centennial, CO (US)

(73) Assignee: Swan Valley Medical, Incorporated, Big Fork, MT (US)

( * ) Notice: Subject to any disclaimer, the term of this patent is extended or adjusted under 35 U.S.C. 154(b) by 626 days.

(21) Appl. No.: 12/239,129

(22) Filed: Sep. 26, 2008

(65) Prior Publication Data
US 2009/0088599 A1     Apr. 2, 2009

Related U.S. Application Data

(60) Provisional application No. 60/975,548, filed on Sep. 27, 2007, provisional application No. 61/038,457, filed on Mar. 21, 2008.

(51) Int. Cl.
*A61M 29/00* (2006.01)
(52) U.S. Cl. .......... 600/184; 606/108; 606/198
(58) Field of Classification Search ........... 606/191, 606/198, 108, 197, 199; 604/104–107, 164.01, 604/164.03, 164.08–164.11, 164.04; 600/201, 600/210, 219, 225
See application file for complete search history.

(56) References Cited

U.S. PATENT DOCUMENTS

| 84,815 A | 12/1868 | Garvin |
|---|---|---|
| 3,241,554 A | 3/1966 | Coanda |
| 3,640,281 A | 2/1972 | Robertson |
| 3,656,486 A | 4/1972 | Robertson |
| 3,920,023 A | 11/1975 | Dye et al. |

(Continued)

FOREIGN PATENT DOCUMENTS

DE     3211576     10/1983

(Continued)

OTHER PUBLICATIONS

Japanese Patent Office, Notification of Reasons of Refusal for Application No. 2007-511458, Dec. 7, 2010, 1 page.

(Continued)

*Primary Examiner* — Elizabeth Houston
*Assistant Examiner* — Sarah Webb

(57) ABSTRACT

A bladder access apparatus and method of provided access into a bladder through a abdominal wall therewith is provided. The apparatus has an annular body extending between opposite ends with a through passage extending between the ends. A tubular sheath is attached to one end of the body in coaxial alignment with the through passage. The sheath is expandable from a first diameter to an enlarged second diameter. The apparatus has an elongate stylet with a rod sized for receipt in the sheath. The rod has a length greater than the tubular sheath and a diameter substantially the same as the first diameter of the sheath. The apparatus includes a rigid, tubular body having an outer diameter corresponding substantially to the second diameter of the sheath and a rigid, cylindrical member sized for sliding receipt in the tubular body.

16 Claims, 20 Drawing Sheets

U.S. PATENT DOCUMENTS

| | | | |
|---|---|---|---|
| 3,924,633 | A | 12/1975 | Cook et al. |
| 4,557,255 | A | 12/1985 | Goodman |
| 4,596,553 | A | 6/1986 | Lee |
| 4,627,834 | A | 12/1986 | Lee |
| 4,676,780 | A | 6/1987 | Lee |
| 4,716,901 | A | 1/1988 | Jackson et al. |
| 4,875,897 | A | 10/1989 | Lee |
| 4,899,733 | A | 2/1990 | DeCastro et al. |
| 4,995,868 | A | 2/1991 | Brazier |
| 5,019,032 | A | 5/1991 | Robertson |
| 5,059,183 | A | 10/1991 | Semrad |
| 5,152,749 | A | 10/1992 | Giesy et al. |
| 5,183,464 | A | 2/1993 | Dubrul et al. |
| 5,203,773 | A | 4/1993 | Green |
| 5,232,440 | A | 8/1993 | Wilk |
| 5,232,443 | A | 8/1993 | Leach |
| 5,232,451 | A | 8/1993 | Freitas et al. |
| 5,275,166 | A | 1/1994 | Vaitekunas et al. |
| 5,275,611 | A | 1/1994 | Behl |
| 5,290,294 | A | 3/1994 | Cox et al. |
| 5,304,119 | A | 4/1994 | Balaban et al. |
| 5,312,360 | A | 5/1994 | Behl |
| 5,330,497 | A | 7/1994 | Freitas et al. |
| 5,334,185 | A * | 8/1994 | Giesy et al. ............ 604/170.01 |
| 5,348,541 | A | 9/1994 | Lyell |
| 5,356,382 | A | 10/1994 | Picha et al. |
| 5,431,676 | A * | 7/1995 | Dubrul et al. ................ 606/185 |
| 5,490,845 | A | 2/1996 | Racz |
| 5,545,141 | A | 8/1996 | Eld |
| 5,546,958 | A | 8/1996 | Thorud et al. |
| 5,662,676 | A | 9/1997 | Koninckx |
| 5,720,763 | A | 2/1998 | Tovey |
| 5,772,678 | A | 6/1998 | Thomason et al. |
| 5,827,319 | A | 10/1998 | Carlson et al. |
| 5,836,913 | A | 11/1998 | Orth et al. |
| 5,843,113 | A | 12/1998 | High |
| 5,857,999 | A | 1/1999 | Quick et al. |
| 5,882,340 | A * | 3/1999 | Yoon .................. 604/164.12 |
| 5,935,107 | A | 8/1999 | Taylor et al. |
| 5,971,958 | A | 10/1999 | Zhang |
| 6,030,393 | A | 2/2000 | Corlew |
| 6,099,547 | A | 8/2000 | Gellman et al. |
| 6,162,236 | A | 12/2000 | Osada |
| 6,171,281 | B1 | 1/2001 | Zhang |
| 6,245,052 | B1 | 6/2001 | Orth et al. |
| 6,319,266 | B1 | 11/2001 | Stellon et al. |
| 6,436,119 | B1 | 8/2002 | Erb et al. |
| 6,482,175 | B1 | 11/2002 | Walker |
| 6,524,304 | B1 | 2/2003 | Picou et al. |
| 6,547,761 | B2 | 4/2003 | Liu |
| 6,558,349 | B1 | 5/2003 | Kirkman |
| 6,576,008 | B2 | 6/2003 | Devonec et al. |
| 6,596,001 | B2 | 7/2003 | Stormby et al. |
| 6,616,678 | B2 | 9/2003 | Nishtala et al. |
| 6,629,987 | B1 | 10/2003 | Gambale et al. |
| 6,632,197 | B2 | 10/2003 | Lyon |
| 6,743,207 | B2 | 6/2004 | Elbert et al. |
| 6,796,976 | B1 | 9/2004 | Chin et al. |
| 6,800,084 | B2 | 10/2004 | Davison et al. |
| 6,811,558 | B2 | 11/2004 | Davison et al. |
| 6,893,418 | B2 | 5/2005 | Liu |
| 6,932,829 | B2 | 8/2005 | Majercak |
| 7,179,219 | B2 | 2/2007 | Matlock |
| 7,186,238 | B2 | 3/2007 | Elbert et al. |
| 7,377,897 | B1 | 5/2008 | Kunkel et al. |
| 7,398,781 | B1 * | 7/2008 | Chin ............................ 128/898 |
| 7,614,999 | B2 | 11/2009 | Gellman et al. |
| 2002/0026207 | A1 | 2/2002 | Stellon et al. |
| 2004/0225300 | A1 | 11/2004 | Goldfarb et al. |
| 2005/0143690 | A1 | 6/2005 | High |
| 2005/0171511 | A1 | 8/2005 | High |
| 2006/0052750 | A1 * | 3/2006 | Lenker et al. ............ 604/164.01 |
| 2006/0271065 | A1 | 11/2006 | High |
| 2008/0009797 | A1 | 1/2008 | Stellon et al. |

FOREIGN PATENT DOCUMENTS

| | | |
|---|---|---|
| DE | 3919740 | 12/1990 |
| DE | 202008011708 | 10/2009 |
| EP | 0127261 A1 | 12/1984 |
| JP | 59183766 | 10/1984 |
| WO | 96/22742 | 8/1996 |
| WO | 0219890 | 3/2002 |
| WO | 03/088833 | 10/2003 |
| WO | 2005/109487 | 11/2005 |
| WO | 2009042985 | 4/2009 |
| WO | 2009042988 | 4/2009 |

OTHER PUBLICATIONS

International Search Report, dated Feb. 21, 2007, for International Application No. PCT/US 05/15015, 1 page.

PCT International Search Report and PCT Written Opinion, for International Application No. PCT/US 2008/078053, dated May 25, 2009, 8 pages.

Supplementary European Search Report, dated Sep. 15, 2009, for Application No. EP 05 740 938, 3 pages.

EPO Office Action, dated Jan. 13, 2010, for Application No. 05 740 938, 4 pages.

PCT International Search Report and PCT Written Opinion, for International Application No. PCT/US 2008/078062, dated Mar. 27, 2009, 9 pages.

Marc A. Lowe, M.D. and Alfred J. Defalco, M.D., New Endourologic Technique for Catheter Placement After Turp, Prostatectomy, and Difficult Urethroscopy, Nov. 1992, pp. 461-463, vol. 40, No. 5, Department of Urology, University of Washington, Seattle, Washington.

Autosuture, The New and Innovative VersaStep PLUS 15mm Access Device, website printout dated Jun. 30, 2008, 2 pages, Tyco Healthcare Group LP, United States.

* cited by examiner

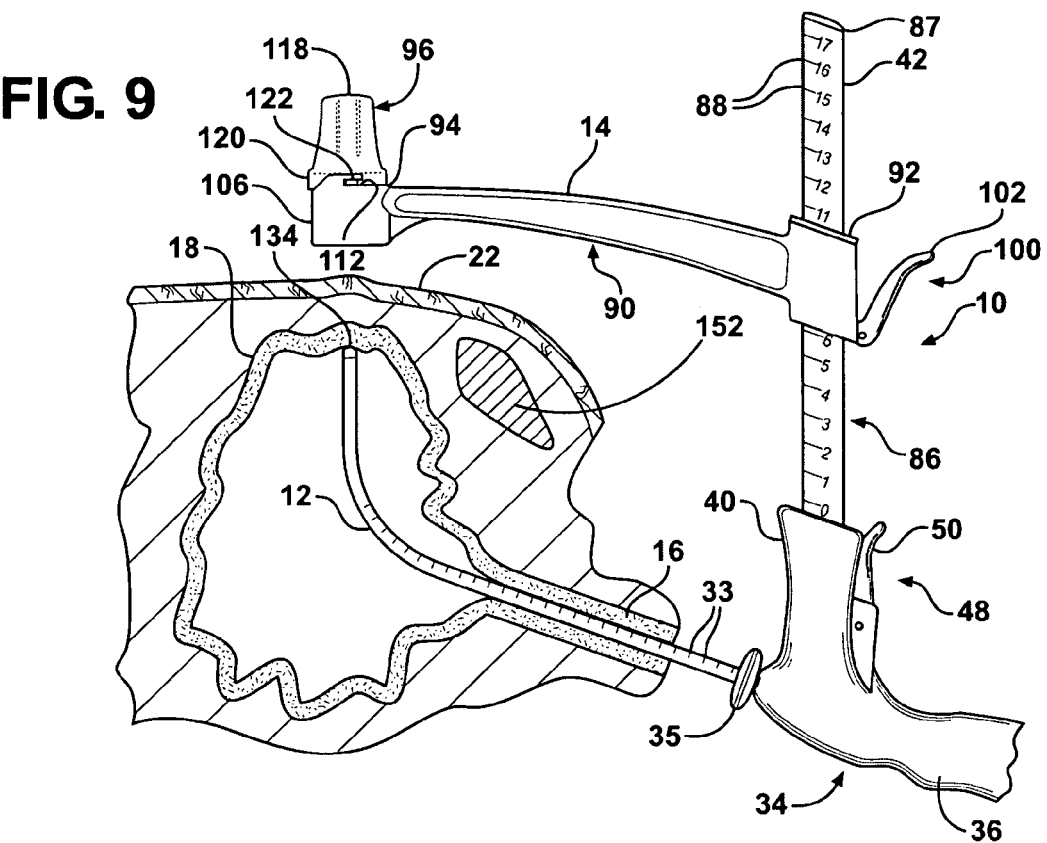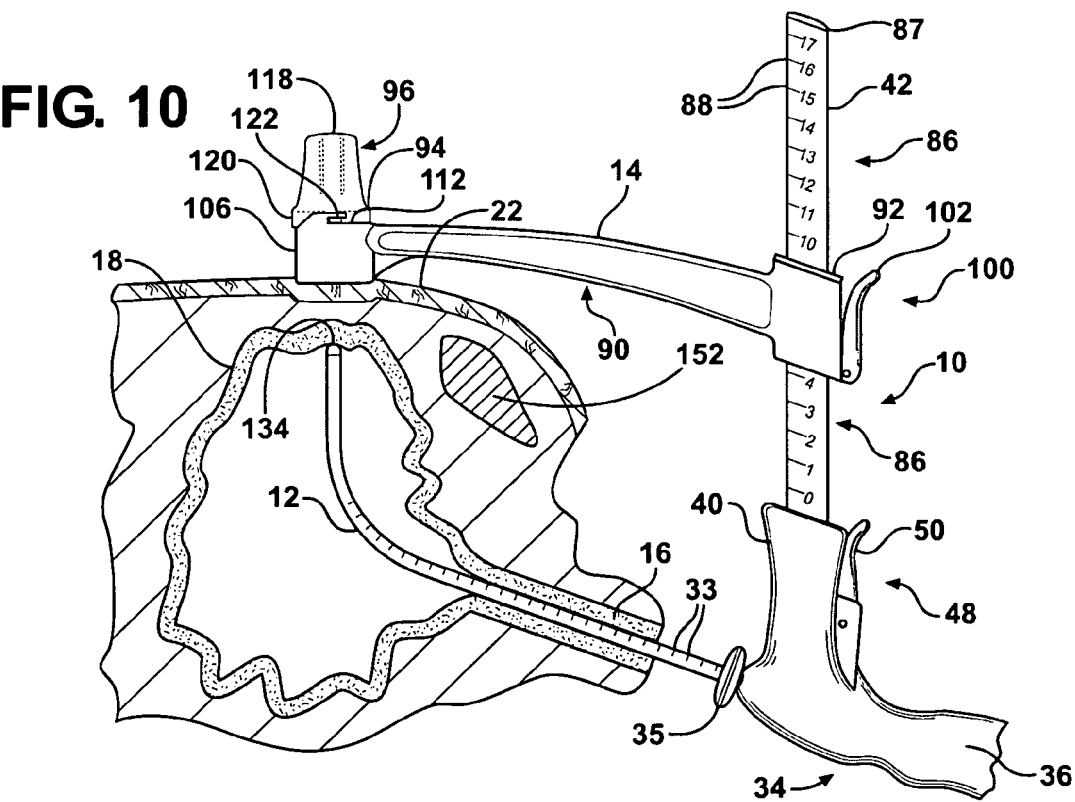

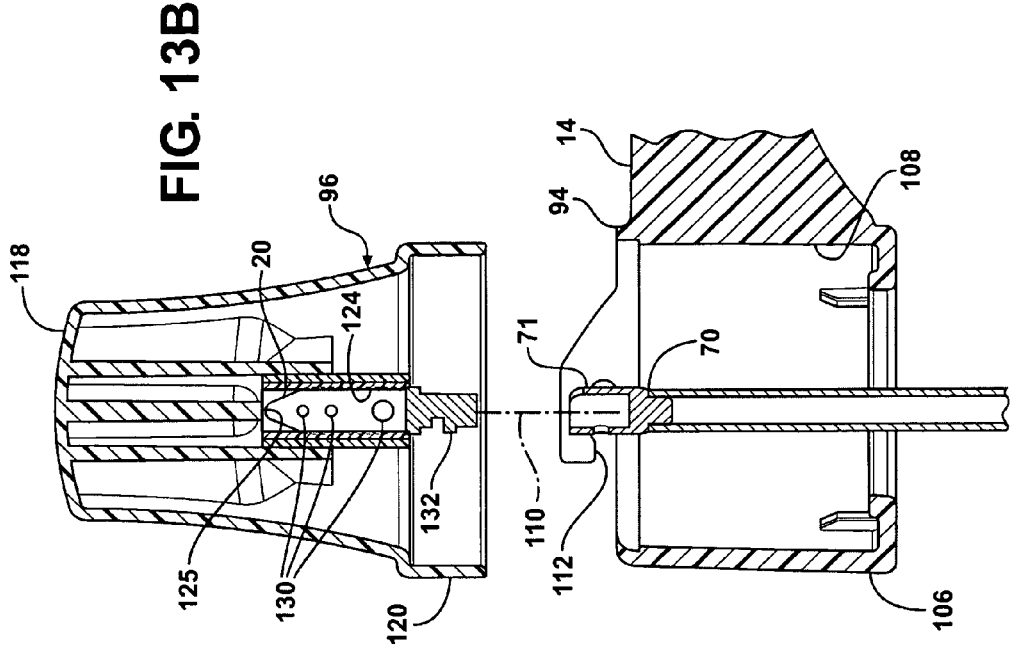
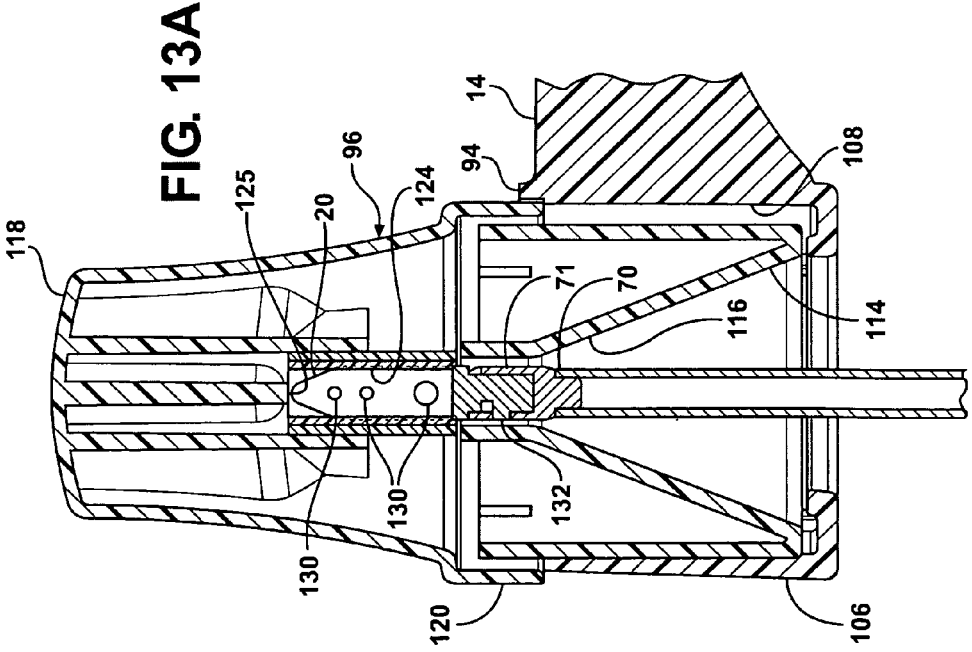

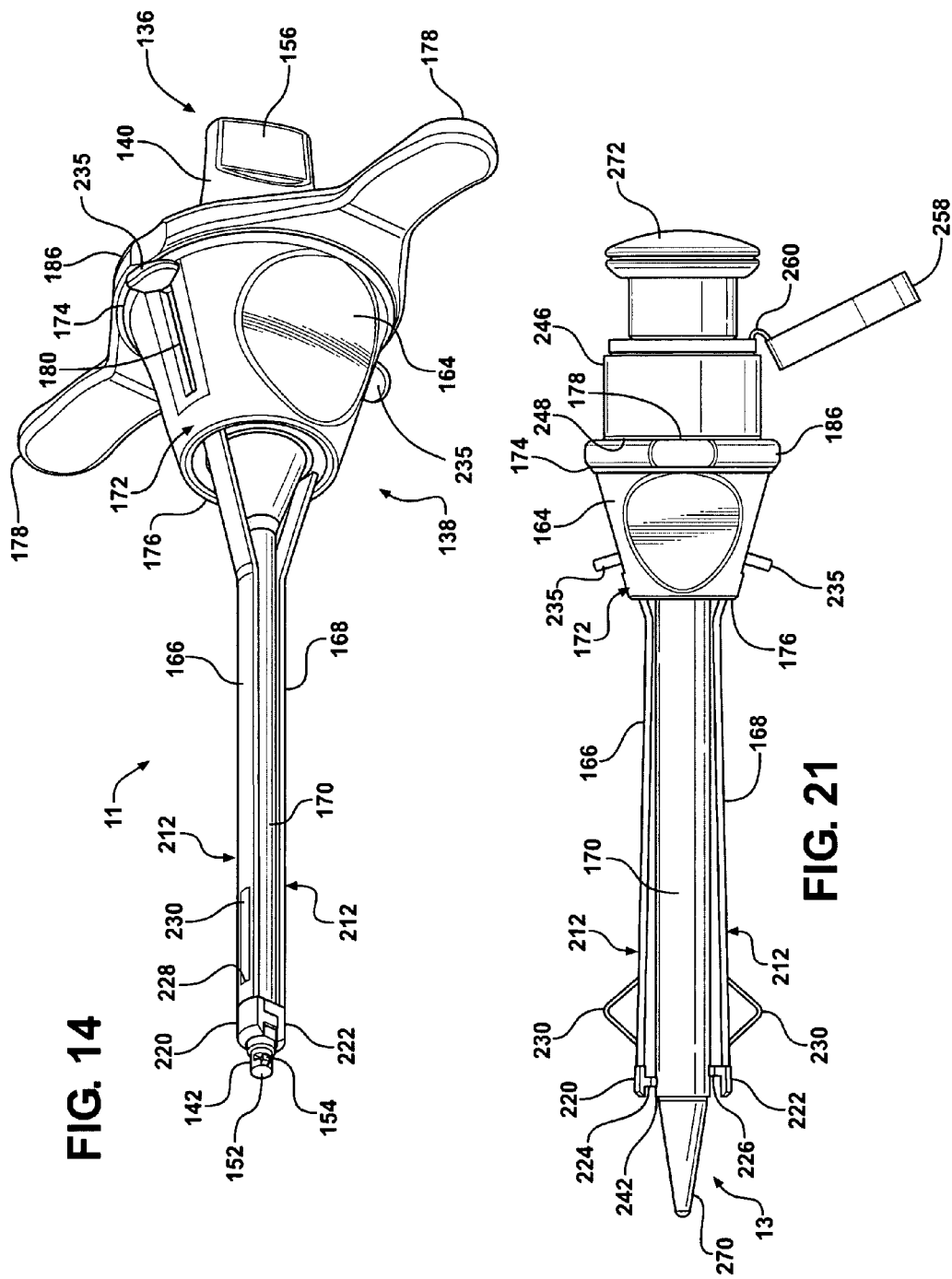

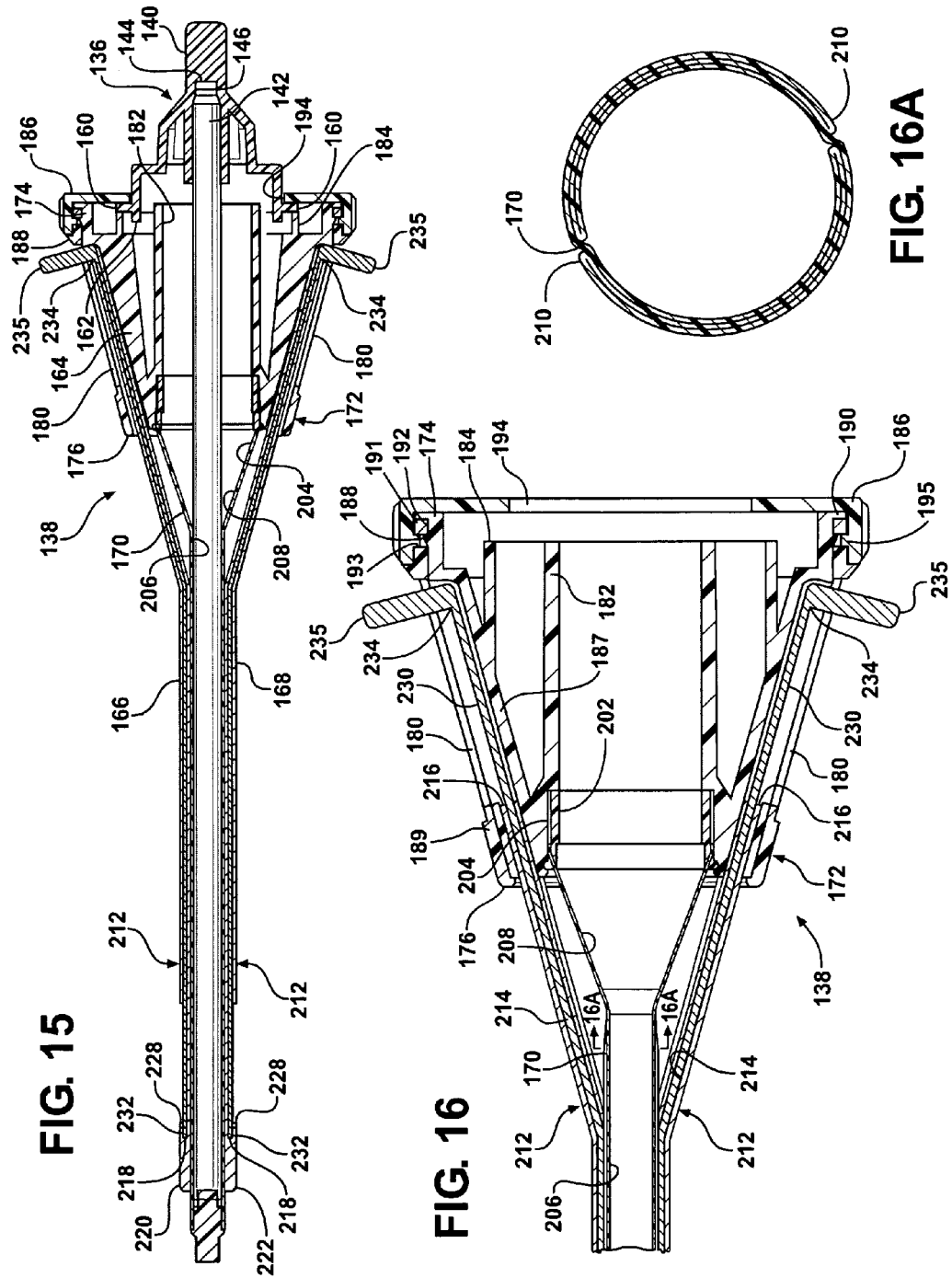

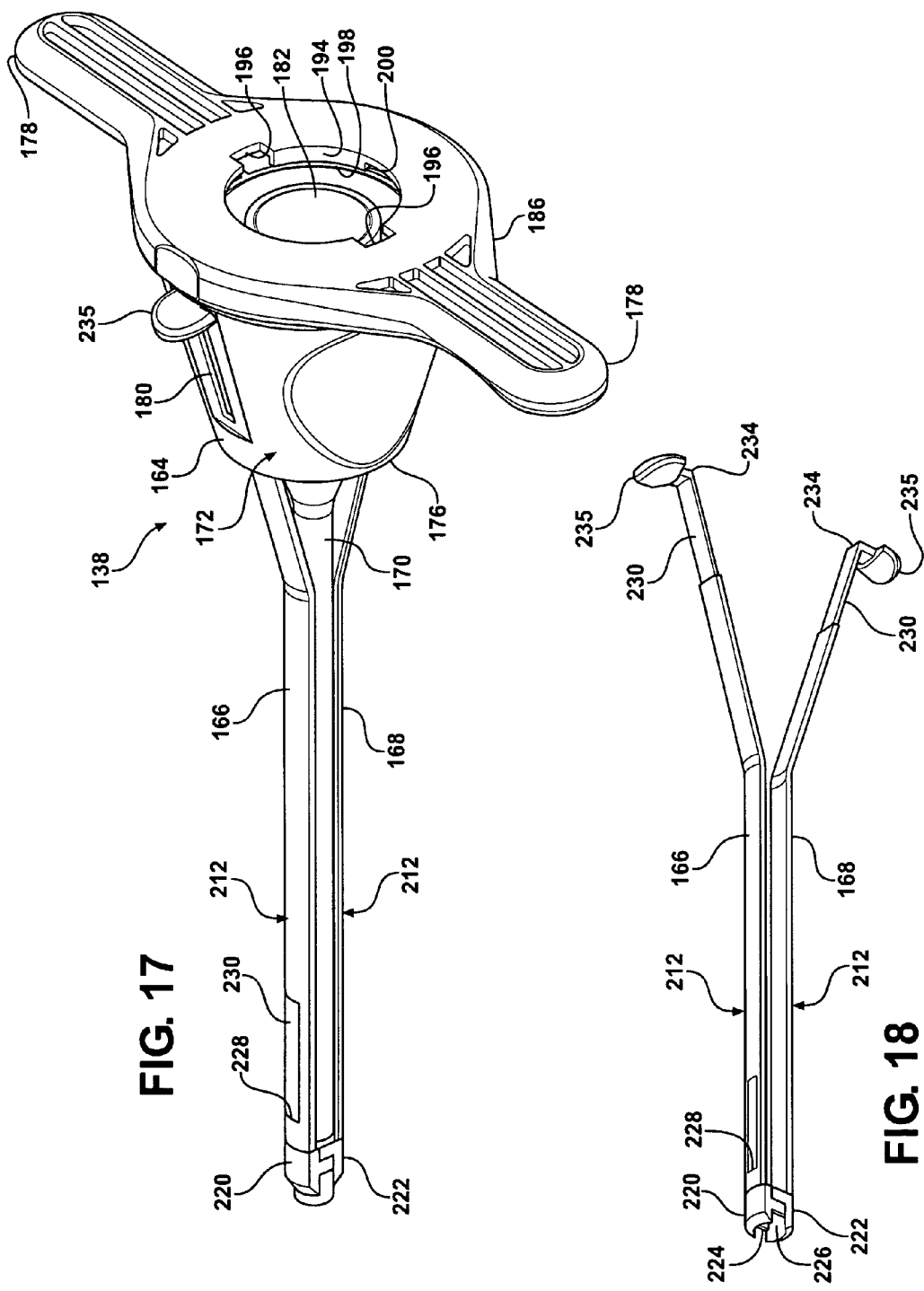

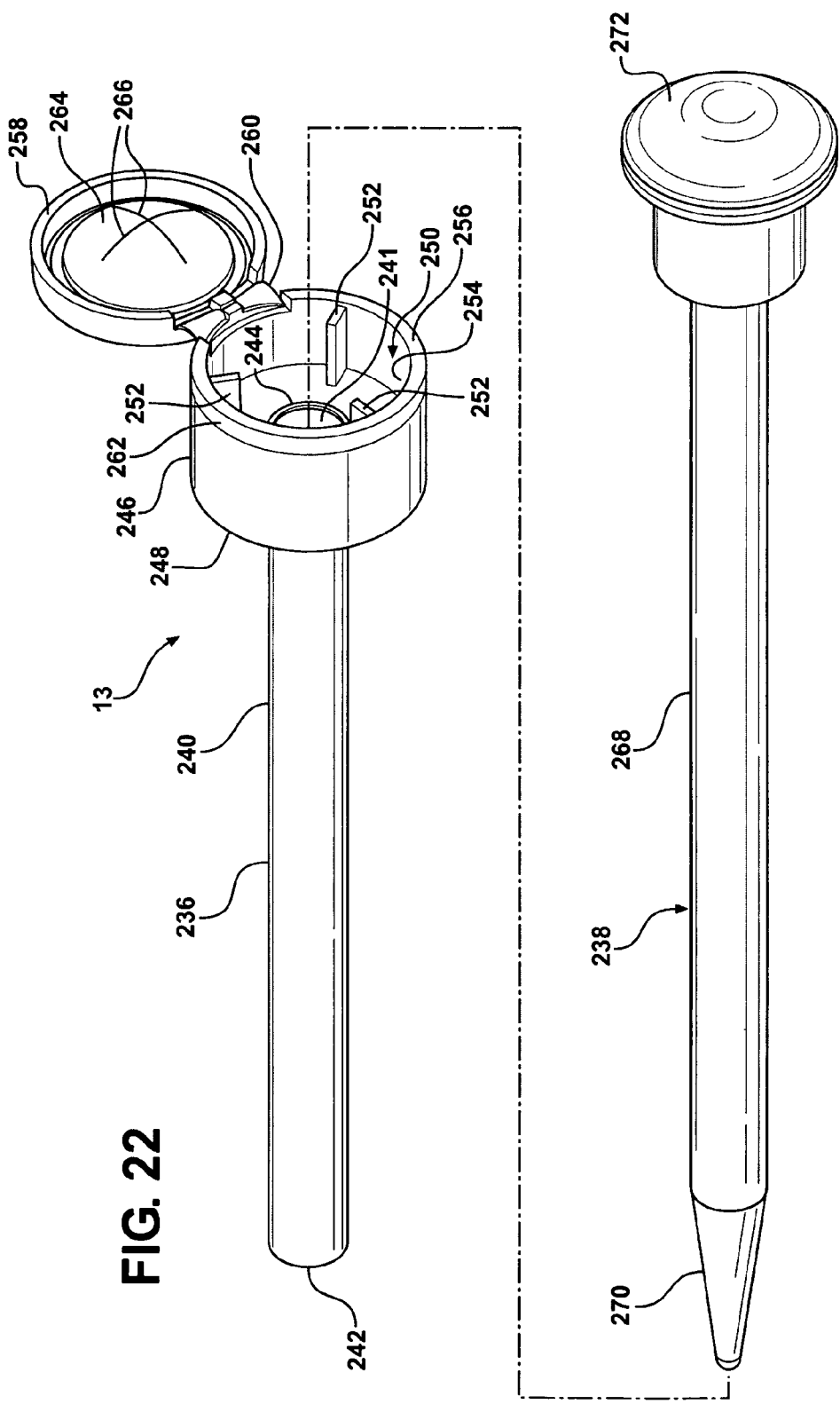

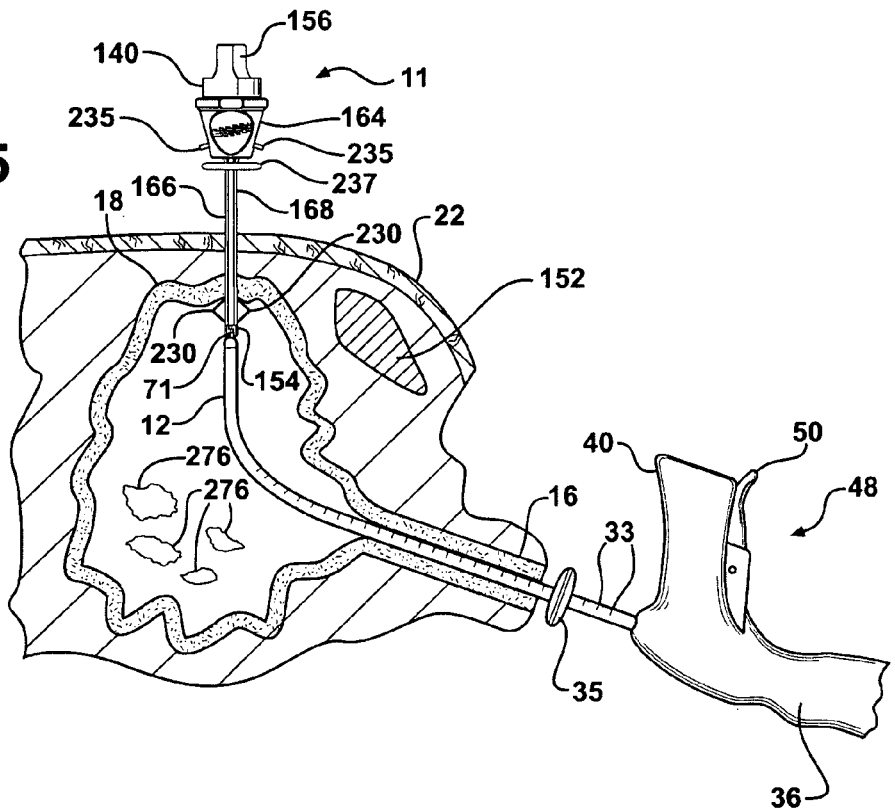
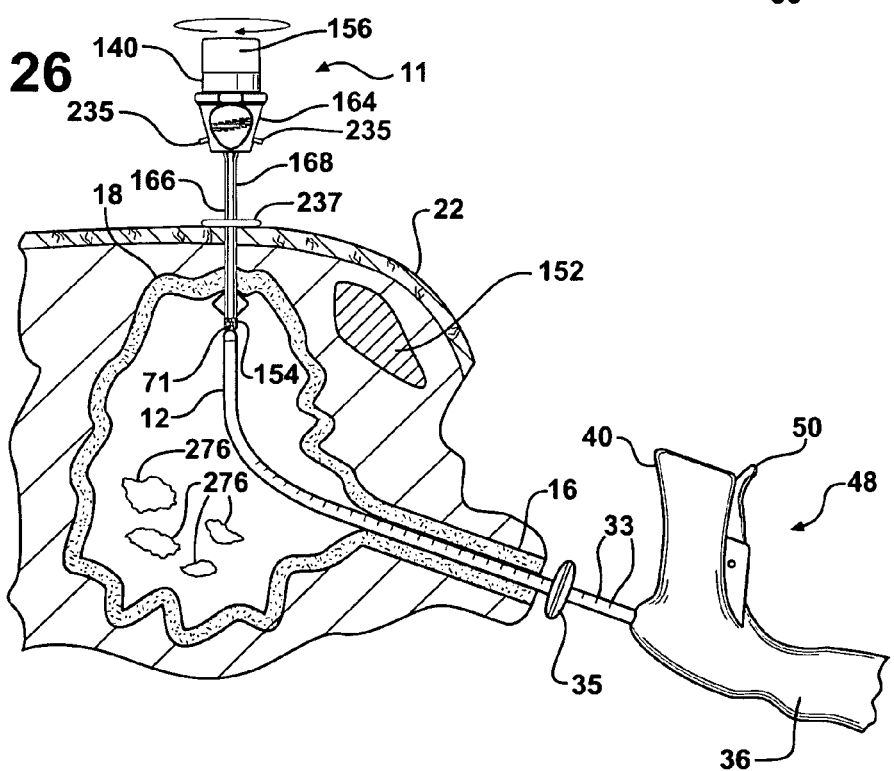

METHOD OF ACCESSING A BLADDER AND ASSOCIATED APPARATUS THEREFOR

CROSS-REFERENCE TO RELATED APPLICATIONS

This application claims the benefit of U.S. Provisional Application Ser. No. 60/975,548, filed Sep. 27, 2007, and U.S. Provisional Application Ser. No. 61/038,457, filed Mar. 21, 2008, both of which are incorporated herein by reference in their entirety.

BACKGROUND OF THE INVENTION

1. Technical Field

This invention relates generally to methods and apparatus for forming a surgical opening, and more particularly to methods and apparatus for forming an opening into a bladder to provide access to the bladder, associated urological procedures and other surgical procedures.

2. Related Art

Bladder calculi (or stones) are common in the population and are presently treated either with open surgery through the abdomen, or transurethrally with the aid of a cystoscope and various fragmentation devices. Minimally invasive surgical therapy for kidney stones was started around thirty years ago, and adaptations of these techniques were applied to bladder calculi surgery just ten years ago. The same instruments used to treat kidney stones also work very well for bladder stones. The surgical challenge has always been to gain access to the bladder using a minimally invasive technique, and to prevent urethral trauma and later formation of urethral stricture (scar tissue).

Two widely-accepted techniques for creating percutaneous bladder access involve mechanical dilation, the most common of which is the "Amplatz" dilators and sheath. The second technique is the use of a special catheter with a balloon capable of enlarging openings percutaneously through the abdominal and bladder walls. Each is accomplished while a urologist observes transurethrally through a cystoscope the devices entering the bladder to be sure that, in the first case, that the Amplatz instruments do not perforate the rectum or vagina, and in the second case, the catheter location is indeed within the bladder instead of outside.

Transurethral bladder calculi treatment, though less invasive as open surgery, carries inherent risks to the patient. Repeated manipulation of instruments in the urethra during the procedure can create significant trauma. Transurethral bladder calculi treatment also can be expensive from the physician's standpoint due to the protracted time required to sufficiently break the stones to be passed through the urethra. The equipment required to break the stones transurethrally can also be expensive, as in the case of the Holmium:YAG laser.

SUMMARY OF THE INVENTION

A bladder access apparatus has an annular body extending between opposite ends with a through passage extending between the ends. The body has a pair of slots diametrically opposite one another and extending lengthwise between the ends. The apparatus further includes a pair of tubular walls extending from one of the ends of the annular body to a pair of free ends. Each of the tubular walls has a hollow channel aligned with one of the slots with an elongated opening extending through the walls with the elongated openings facing away from one another adjacent a respective one of the free ends. Further, an elongate, resilient strip is slidably received in each of the hollow channels with one end of the strips having a gripping member operably attached thereto. Each of the gripping members extends outwardly from one of the slots for sliding movement along the slots between locked and unlocked positions and another end of the strips extends beyond a respective one of the windows. A portion of each strip extends outwardly from a respective one of the windows upon moving the gripping member toward the locked position, with the portions being retracted back into the respective window upon moving the gripping member toward the unlocked position. An expandable tubular sheath is attached to the body and extends between the tubular walls. The apparatus further includes a rigid, tubular body configured for receipt in the tubular sheath to expand the sheath and a rigid, cylindrical member sized for sliding receipt in the tubular body.

In accordance with another aspect of the invention, a bladder access apparatus is provided having an annular body extending between opposite ends with a through passage extending between the ends with an tubular sheath being attached to one end of the body in coaxial alignment with the through passage. The sheath has a first diameter and is expandable to an enlarged second diameter. The apparatus further includes an elongate stylet having a rod sized for receipt in the sheath. The rod has a length greater than the tubular sheath and a diameter substantially the same as the first diameter of the sheath. Further, the apparatus includes a rigid, tubular body having an outer diameter corresponding substantially to the second diameter of the sheath and a rigid, cylindrical member sized for sliding receipt in the tubular body.

In accordance with another aspect of the invention, a method of providing access into a bladder through a abdominal wall is provided. The method includes forming an opening through the bladder and the abdominal wall with a transurethral, suprapubic apparatus and extending an end of the transurethral, suprapubic apparatus outwardly from the abdominal wall. Further, providing a rod having an expandable sheath disposed thereon; attaching an end of the rod to the end of the transurethral, suprapubic apparatus, and then, pulling the rod and sheath into the bladder by withdrawing a portion of the transurethral, suprapubic apparatus outwardly from the urethra. Then, while the connected ends are in the bladder, disconnecting the end of the rod from the end of the transurethral, suprapubic apparatus. Further, pulling the rod out of the sheath, and pushing a rigid, tubular body through the sheath and expanding the sheath with one end of the tubular body remaining outside the abdominal wall and an opposite end of the tubular body being received in the bladder.

Accordingly, the technique and apparatus employed and described below and shown in the figures is much more rapid and also much more reliable than all current methods of tract creation. Further, with the working sheath being about 36-40 French (12 mm), it is the largest available to date. It is estimated that the procedures performed in accordance with the invention will be shortened by up to 70%, and hospital stay will be shortened.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 9 is a view similar to FIG. 8 showing an alignment guide arm and capture cup of the apparatus positioned above an abdominal wall;

FIG. 10 is a side view showing the capture cup lowered into contact with the abdominal wall;

FIG. 13A is an enlarged cross-sectional view of the capture cup showing the cutting tip attached to the advancement rod and captured in the capture cup;

FIG. 13B is an enlarged cross-sectional view of the capture cup showing the capture cup and the cutting tip removed from the advancement rod and captured in the capture cup;

FIG. 14 is a perspective view of a dilator assembly;

FIG. 15 is a cross-sectional view of the dilator assembly;

FIG. 16 is an enlarged cross-sectional view of a housing of the dilator assembly;

FIG. 16A is a cross-sectional view taken generally along line 16A-16A of FIG. 16;

FIG. 17 is a rear perspective view of the housing of FIG. 16;

FIG. 18 is a perspective view of a dilator arm assembly dilator assembly;

FIG. 21 is a side view of the dilator assembly with the stylet removed therefrom and showing a pair of dilator tabs deployed and further showing an obturator-cannula assembly disposed therein;

FIG. 22 is an exploded perspective view of the obturator-cannula assembly;

FIG. 25 is a view similar to FIG. 24 showing the stylet rod being pulled further into the bladder and the dilator tabs deployed within the bladder;

FIG. 26 is a view similar to FIG. 25 showing the stylet handle being rotated to disconnect the end of the stylet rod from the collet of the advancement member;

DETAILED DESCRIPTION OF PRESENTLY PREFERRED EMBODIMENTS

Figure 1:
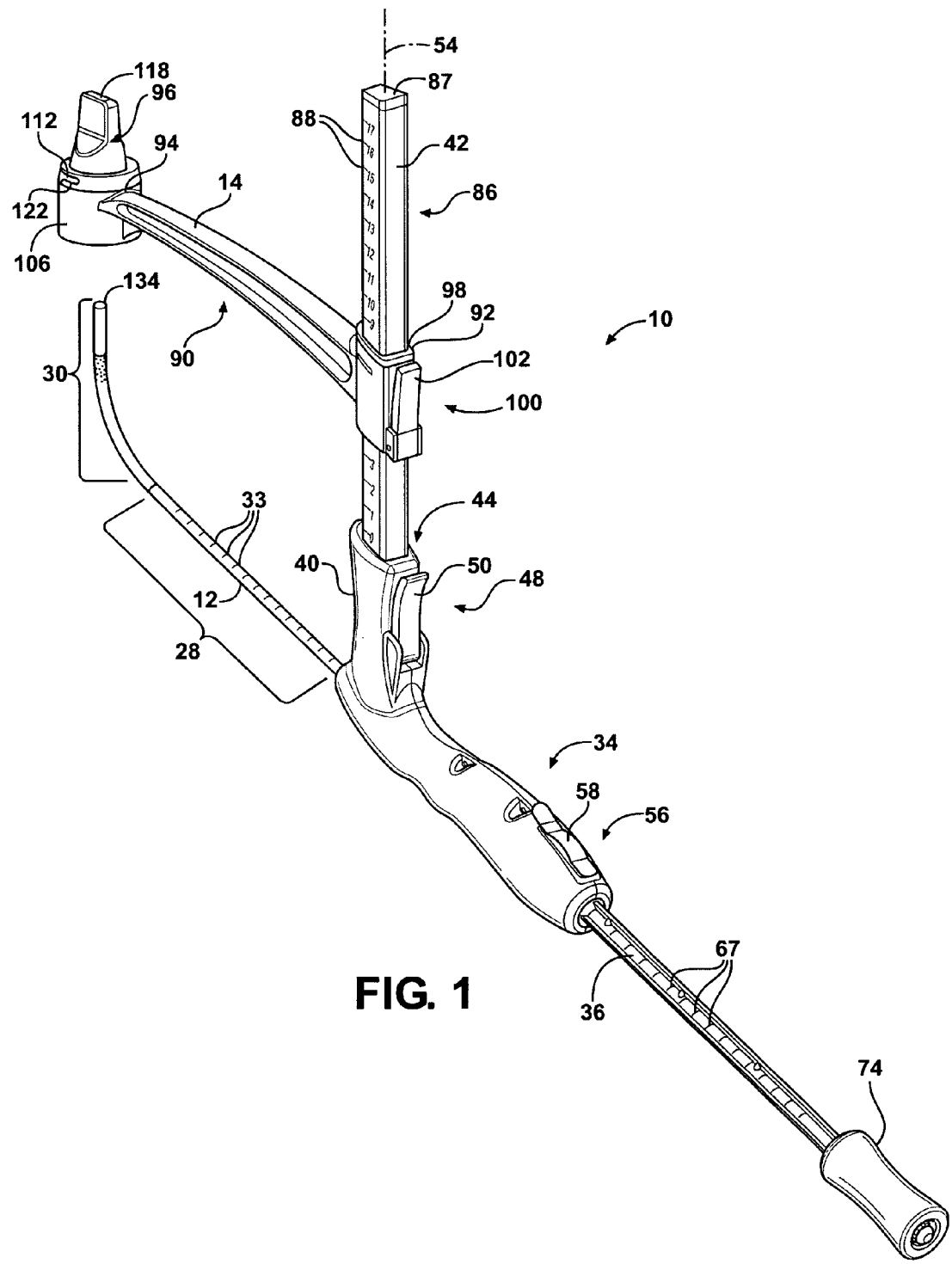
FIG. 1 is a perspective view of a transurethral suprapubic cystostomy apparatus constructed in accordance with one presently preferred embodiment of the invention.
Figure 2:
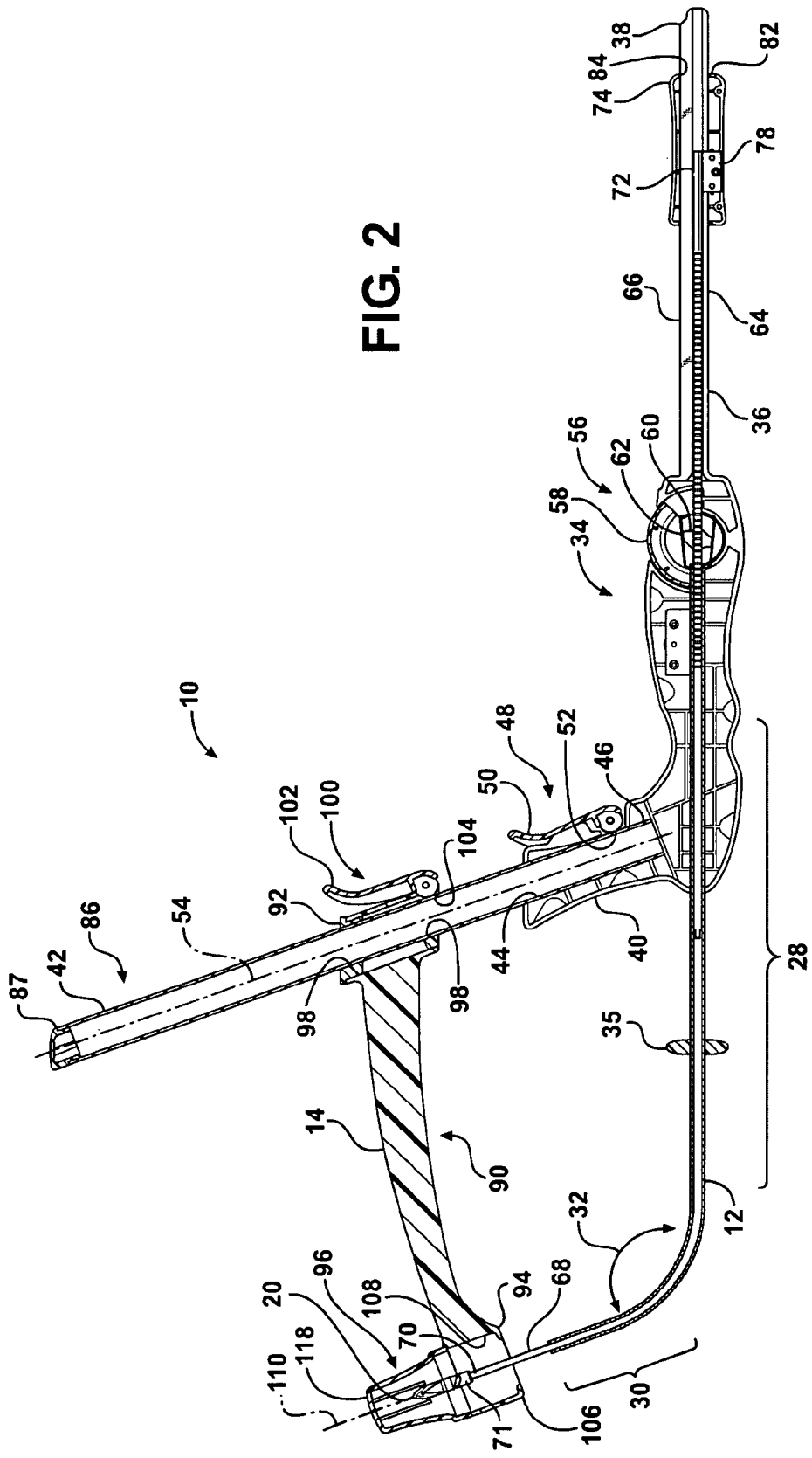
FIG. 2 is a cross-sectional side view of the apparatus of FIG. 1.
Figure 3:
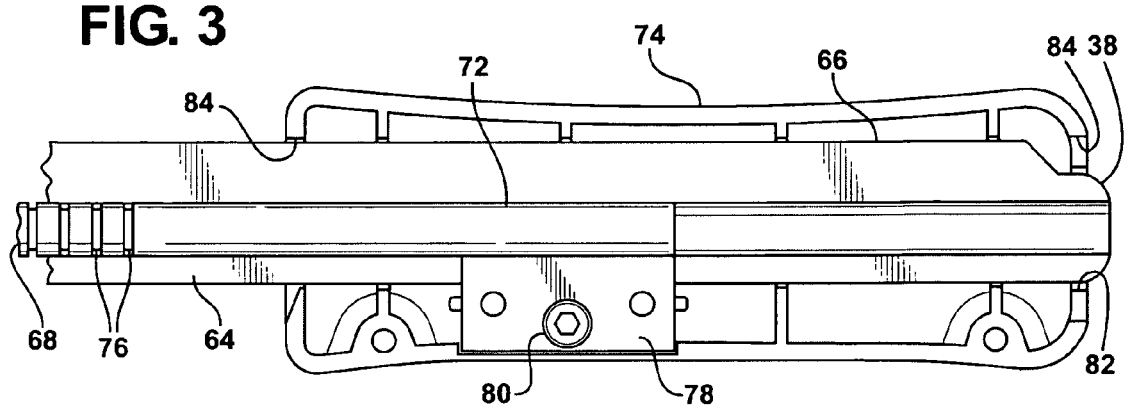
FIG. 3 is an enlarged cross-sectional side view of a rear handle of the apparatus of FIG. 1.
Figure 4:
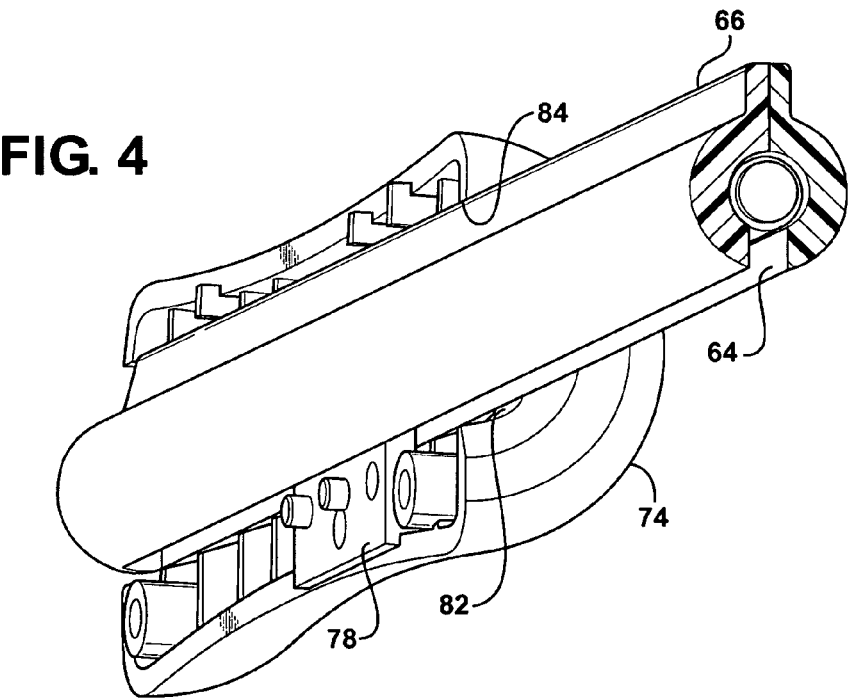
FIG. 4 is an enlarged fragmentary perspective view of a rear handle of the apparatus of FIG. 1.
Figure 5:
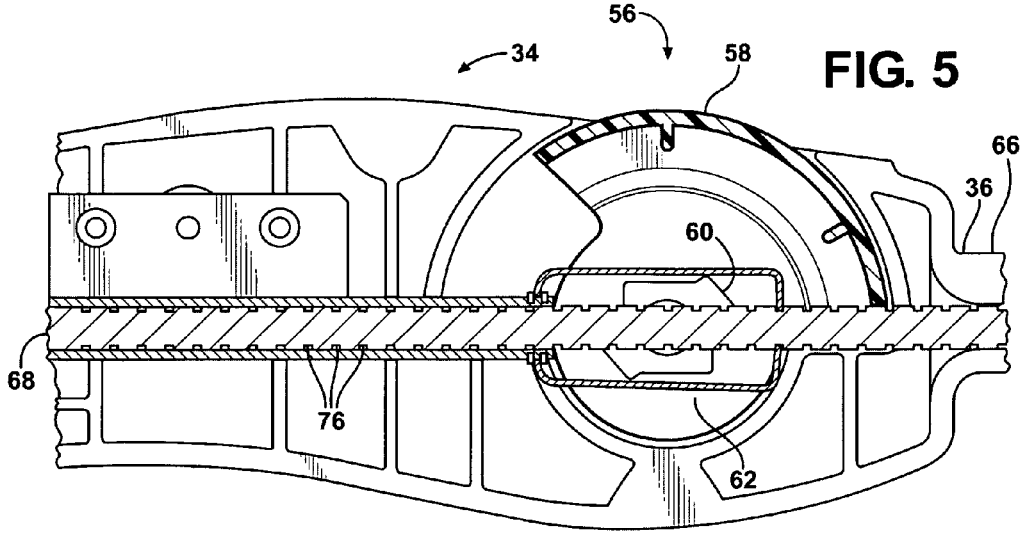
FIG. 5 is an enlarged cross-sectional side view of the front handle shown in a locked position.
Figure 6:
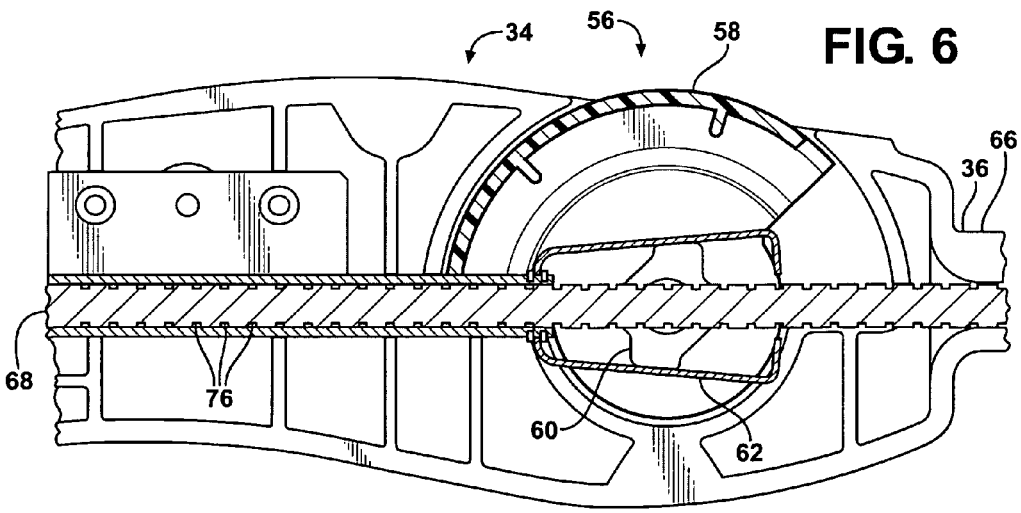
FIG. 6 is an enlarged cross-sectional side view of the front handle shown in an unlocked position.
Figure 7:
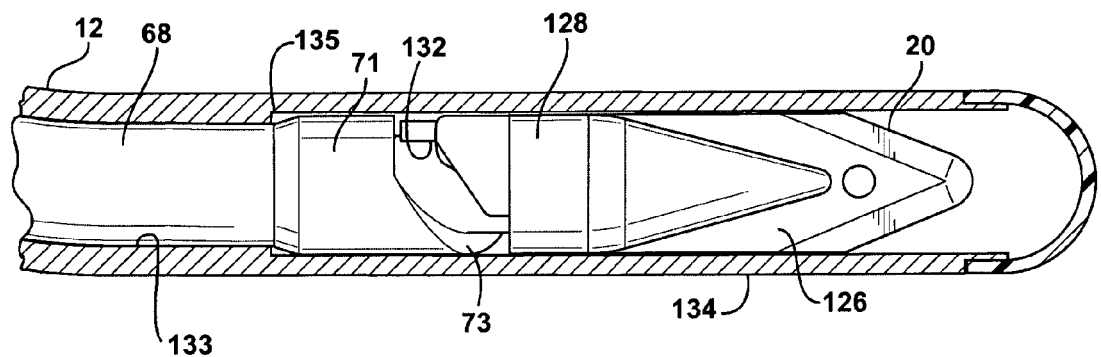
FIG. 7 is an enlarged side view of a cutting tip attached to a collet of an advancement member of the apparatus of FIG. 1.

Referring in more detail to the drawings, FIGS. 1 and 2 illustrate a suprapubic transurethral cystostomy apparatus 10 constructed in accordance with one aspect of the invention, while FIGS. 14 and 22 illustrate components of a bladder access apparatus or assembly, including a dilator assembly 11 and an obturator-cannula assembly 13, constructed in accordance with another aspect of the invention. It should be recognized that other embodiments that perform a similar function, in a generally similar way, are contemplated to be within the scope of the invention. For example, the apparatus 10, its associated individual components, and the assemblies 11, 13 can be modified, while having a generally similar construction, and can be further modified, such as to accommodate any size male or female patient, including obese and morbidly obese patients, for example. Of course, it will be recognized by those skilled in the art that female and male organs, particularly the urethra, are shaped differently and have differing lengths, and so, the construction of the apparatus 10 can be varied to accommodate those differences. The apparatus 10 includes an elongate hollow tubular body, generally referred to as a sound 12, and an elongate alignment guide arm 14 adapted for operable attachment in a predetermined position relative to the sound 12. The sound 12 is configured for insertion through a urethra 16 (FIGS. 8-18) into a bladder 18, while the alignment guide arm 14 remains outside the patient to indicate the precise exit location of a trocar, referred to hereafter as a cutting tip 20, extending from a the sound 12 through an abdominal wall 22 of the patient. In addition to indicating the precise exit location of the cutting tip 20 through the abdominal wall 22, the alignment guide arm 14 can be positioned to abut the abdominal wall 22 to provide a clamping action against the abdominal wall 22, thereby holding the instrument in place and providing tensile reinforcement of the patient's surface skin to allow the cutting tip 20 to cleanly pierce the skin as it extends outwardly through abdomen without stretching or tearing of the skin. As such, the alignment guide arm 14 allows the surgeon to readily identify the precise location of the cutting tip 20 while in its blind location within the bladder 18, thereby enabling the surgeon to puncture a surgical pathway, referred to hereafter as an opening 24, through the bladder 18 and the abdomen wall 22 at a precise and intended location. Accordingly, the surgeon is provided with an increased level of confidence that the opening 24 formed by the cutting tip 20 is at the desired location, will be clean without tearing, and is further assured that inadvertent damage to internal organs, such as the bowel, is avoided. Upon forming the opening 24, a portion of the dilator assembly 11 (FIGS. 23-29) can be inserted through the opening 24 and into the bladder 18 under guided control of the apparatus 10, and then the obturator-cannula assembly 13 can be disposed through the dilator assembly 11 to facilitate performing surgical procedures requiring access to the inside of the bladder (FIGS. 30-33).

Figure 8:
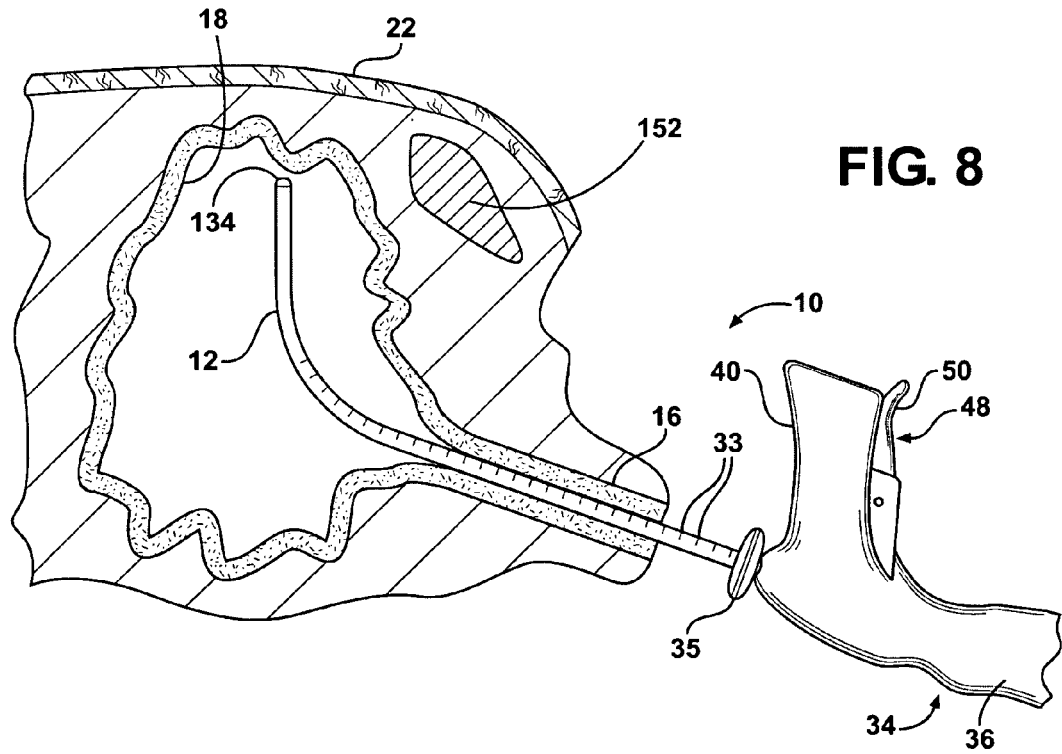
FIG. 8 is a side view of a patient's urethra and bladder showing a sound of the apparatus inserted therein.

As best shown in FIGS. 1 and 2, the sound 12 has a proximal portion 28 and a distal portion 30, with the distal portion 30 being configured for insertion into the bladder 18 through the urethra 16 (e.g., FIG. 8). The proximal portion 24 and the distal portion 26 have respective linear sections that are inclined relative to one another at a predetermined and generally fixed obtuse angle of inclusion 32, such that the angle between the respective linear sections remains generally fixed in use. The proximal portion 28 can have measured indicator markings 33 to indicate to the surgeon the depth of insertion of the sound 12 into the urethra 16. In addition, a penetration depth marker, also referred to as an indicator slide 35 can be disposed on the proximal portion 28 to assist in readily identifying the depth and location of the sound 12 within the bladder 18 during the procedure. The sound 12 is constructed from a material that can be readily sterilized, such as stainless steel, by way of example and without limitation. It should be recognized that other materials which can be readily sterilized are contemplated and incorporated herein within the scope of the invention, including plastics materials, for example. The sound 12, although constructed from a material capable of being sterilized, is preferably constructed as a disposable, single use instrument.

The proximal portion 28 is fixedly connected to a front handle 34 which has a straight, tubular body 36 extending rearwardly away from the sound 12 to an end 38. The front handle 34 provides a reliable and comfortable location for grasping and manipulating the sound 12. The front handle 34 can be provided having any suitable shape and configuration, depending on the requirements of the surgeon. For example, the front handle 34 can be ergonomically designed for left and right handed physicians and designed for optimal manipulation, control and orientation of the sound 12 while preventing hand slippage when wet and in contact with surgical gloves. Accordingly, it is contemplated that the front handle 34 can be provided having different shapes and contours, as desired. The front handle 34 and tubular body 36 can be molded as single piece halves and then subsequently joined, such as via fasteners, an adhesive or via welding, for example. Of course, the front handle 34 and tubular body 36 can be formed using any suitable materials and processes.

The front handle 34 has an upstanding housing, referred to hereafter as mount sleeve 40, configured for releasable attachment of a straight slide arm, referred to hereafter as mast 42, thereto. As best shown in FIG. 2, the mount sleeve 40 has a pocket 44 sized for close receipt of one end 46 of the mast 42 therein. To facilitate fixing the end 46 of the mast in the pocket 44, the mount sleeve 40 has a releasable mast locking mechanism 48, represented here, by way of example and without limitation, as an over-center cam latch lever 50. The cam latch lever 50 has a cam surface 52 that frictionally engages the mast 42 when the lever 50 is in a depressed, locked position, thereby maintaining the mast 42 in a fixed position within the pocket 44. Otherwise, when the lever 50 is pivoted to a raised, unlocked position, the cam surface 52 is moved out of engagement with the mast 42, thereby allowing the mast 42 to be removed from the pocket 44. The pocket 44 is configured to extend along a straight, linear axis 54, whereby the mast 42, upon being locked within the pocket 44 also extends along the axis 54. The axis 54 is oriented to extend substantially parallel to the distal portion 30 of the sound 12. Accordingly, upon fixing the mast 42 in the mount sleeve 40, the mast 42 and the distal portion 30 of the sound 12 extend parallel or substantially parallel to one another. The angle of the mast 42 extending from the front handle 34 is configured to properly align the alignment guide arm 14 and a capture cup assembly 96 in the proper position to accept the cutting tip 20. This is of great assistance to the surgeon, as the surgeon otherwise would not have a visual location of the cutting tip 20 when inside the bladder 18.

The front handle 34 further includes a cutting tip locking mechanism 56, represented here, by way of example and without limitation, as having a rotatable brake knob or wheel 58, a cam member 60 fixed to the wheel 58 for conjoint rotation therewith, such as by being formed as a single piece of material therewith, and a spring member, referred to hereafter as a brake spring 62. When the wheel 58 is rotated to a locked position, the cutting tip 20 is fixed against movement relative to the sound 12, and when rotated to an unlocked position, the cutting tip 20 is movable relative to the sound 12, discussed further below.

The tubular body 36 extends rearwardly from the front handle 34 a predetermined distance sufficient to provide the range of movement of the cutting tip 20 desired. It should be recognized that the required range of movement of the cutting tip 20 will generally be less for a normal sized patient than for an obese or morbidly obese patient, and that the range of movement of the cutting tip 20 can be provided to accommodate any size patient. The tubular body 36 has tubular wall with an elongate slot 64 extending along its length, wherein the length of the slot 64 corresponds at least to the desired distance of travel of the cutting tip 20. The slot 64 is represented here as extending of the full length of the tubular body 36 along a bottom side thereof. The wall of the tubular body 36 is also represented, by way of example and without limitation, as having an upstanding rib 66 extending along an upper side of the wall diametrically opposite the slot 64. The upper side of the tubular wall preferably has measured scale markings 67 to indicate to the surgeon the distance the cutting tip 20 is extended, discussed further below.

The apparatus 10 further includes an advancement member 68, represented here as a flexible coil rod or spring member, with a distal end 70 being operably attached to the cutting tip 20 and a proximal end 72 being attached to a rear handle 74 of the apparatus 10. The distal end 70 is represented here as having a connector 71 for selective, releasable attachment of the cutting tip 20 thereto. The connector 71 is a modified bayonet-type connector, for example, having at least one ramped, spiral shaped entry slot 73 terminating at a recessed lock detent. The proximal end 72 is fixed to the rear handle 74, such as by generally narrow connector plate 78 sized to slide through the slot 64. The connector plate 78 can be fixed to the advancement member 68, such as by a weld joint, for example, and to the rear handle 74 via a fastener 80, for example. The advancement member 68 can be provided of any suitable material flexible enough to traverse the bend in the sound 12 between the proximal portion 28 and the distal portion 30, while being rigid enough to maintain a straight cutting path through the bladder 18 and abdominal wall 22, such as stainless steel or spring steel, for example. The advancement member 68 can further be provided as a single piece of material or multiple pieces of material joined to one another. The advancement member has a plurality of circumferential notches 76 spaced uniformly from one another along a proximal or rear portion thereof for operable locking engagement with the brake spring 62. Preferably, the notches 76 extend over the full portion that traverses beneath the cutting tip lock mechanism 56, thereby allowing the cutting tip 20 to be locked in a fully retracted position and in a fully extended position, as well as over a plurality of locations between the fully retracted and extended positions.

The rear handle 74 can be provided having any suitable shape and configuration. For example, the rear handle 74 can be ergonomically designed for left and right handed physicians and designed for optimal manipulation, control and orientation of the advancement member 68 and cutting tip 20 while preventing hand slippage when wet and in contact with surgical gloves. The rear handle 74 can be molded as single piece halves, with the halves being subsequently joined, such as via fasteners, an adhesive or via welding, for example, and can be formed using any suitable materials and processes. The rear handle 74 is formed with an through passage 82 sized for close sliding receipt over the tubular body 36. The passage 82 can be provided with a recessed notch 84 sized to receive the upstanding rib 66 therein, thereby preventing rotation of the rear handle 74 about the tubular body 36. This prevents unwanted rotation of the cutting tip 20 while forming the opening through the tissue.

The mast 42 has a straight, elongate body 86 extending between the end 46 received in the pocket 44 of the front handle 34 and an opposite end 88. The body 86 preferably has measured scale markings 88 to facilitate indicating to the surgeon the distance over which the cutting tip 20 extends through the abdomen of the patient. The body 86 can be formed as a solid body or a hollowed body using any desired process, such as extrusion, for example, and can be formed of a polymeric or metal material, as desired. The body 86 is represented here as being generally rectangular in lateral cross-section, although any cross-sectional geometry could be used. The body 86 can be provided of any suitable length, and preferably has a length between about 15-20 inches, thereby allowing suitable adjustment of the alignment guide arm 14 on morbidly obese patients.

The alignment guide arm 14 has body 90 that extends between a first end 90 configured for sliding receipt along the mast 42 and an opposite second end 94 configured for attachment to a capture cup 96. As such, the end 90 has a through opening 98 configured for close sliding receipt of the mast body 90. Accordingly, the through opening is shaped having a similar cross-sectional geometry as the mast body 90, though slightly larger than the mast body 90. To facilitate releasably locking the alignment guide arm 14 in a desired fixed position along the mast 42, the first end 90 has a releasable arm locking mechanism 100, represented here, by way of example and without limitation, as an over-center cam latch lever 102. The cam latch lever 102 has a cam surface 104 that frictionally engages the mast 42 when the lever 102 is in a depressed, locked position, thereby maintaining the alignment guide arm 14 in a fixed position along the mast body 86 at the desired position. Otherwise, when the lever 102 is pivoted to a raised, unlocked position, the cam surface 104 is moved out of engagement with the mast body 86, thereby allowing the mast 42 to be slid along the length of the mast body 86.

The second end 94 has a semi-annular or annular housing 106 providing a through passage 108 of a predetermined diameter that extends along an axis 110 that is coaxial with the distal portion 30 of the sound 12 when then alignment guide arm is attached to the mast 42. The housing 106 is further represented here, by way of example and without limitation, as having an upper surface with one or more lateral slots 112 configured to releasably receive the capture cup 96. To facilitate guiding the cutting tip 20 into the capture cup 96, the through passage 108 of the housing 106 can be provided having a funnel shape with an enlarged diameter 114 located adjacent a bottom surface of the housing 106 and a reduced diameter 116 located adjacent the upper surface of the housing 106.

The capture cup 96 has a closed upper portion 118 configured to be easily grasped and rotated, and is represented here, by way of example and without limitation, as having a generally rectangular wall with opposite sides easily graspable between a thumb and index finger. A generally cylindrical, annular wall 120 depends from the upper portion 118, wherein the annular wall is sized for close sliding receipt in the housing 106 of the alignment guide arm 14. Further, the capture cup 96 has one more fingers 122 extending laterally outwardly for sliding receipt in the slots 112 of the housing 106. The fingers 122 extend outwardly to engage the upper surface of the housing 106, and are received in the slots 112 by rotating the capture cup 96 relative to the housing 106. Accordingly, upon rotating the capture cup 96 in one direction, the fingers 122 slide in the slots 112 and engage a bottom surface of the slots, wherein the capture cup is releasable locked to the housing 106, and upon rotating the capture cup 96 in the opposite direction, the fingers 122 exit the slots 112, wherein the capture cup 96 can be removed from the housing.

To facilitate capturing the cutting tip 20 in the capture cup 96, a bore or cavity of the capture cup 96 can be provided with an annular elastomeric wall or sleeve 124, such as an silicone tubing, for example, wherein the sleeve 124 has a slightly reduced diameter from the outer periphery of the cutting tip 20 to cause the cutting tip 20 to cut into the sleeve 124 upon being inserted therein, thereby being captured within the capture cup 96 for hands free disposal. To provide assurance that the cutting tip 20 in fully inserted in the capture cup 96, a stop surface 125 can be provided to abut the cutting tip 20, thereby acting as a positive stop to limit the distance the cutting tip 20 can be inserted into the capture cup 96. Although the capture cup 96 is shown having the fingers 122 for releasable receipt in the slots 112, other attachment mechanisms are contemplated herein, such as a threaded attachment or the capture cup could be formed as a single piece of material with the alignment guide arm 14. To further facilitate releasing the cutting tip 20, a plurality of ribs can extend radially inwardly from the inner surface of the sleeve 124 to provide a bearing surface against the flat cutting blade as a 'stop' when rotating the capture cup 96. This further assures the cutting tip 20 will be rotated conjointly with the capture cup 96 while rotating the capture cup 96.

The cutting tip 20 is constructed having a metal cutting member 126 and a connector 128 depending therefrom. The cutting member 126 is illustrated as having one or more openings 130 to facilitate attachment of the cutting member 126 to the connector 128. The connector 128 can be formed of an polymeric material, and further, can be molded, such as in an injection molding process, for example, to the cutting member 126. The connector 128 has a corresponding number of bayonets or fingers 132 extending laterally outwardly for sliding receipt in the ramped slots 73 in the connector 71. The fingers 132 are configured to lock releasably in the slots by deflecting into the recessed detents at the end of the ramped slots 73, and to deflect out of the detents upon applying a suitable torque to the cutting member 126 via rotation of the capture cup 96. The cutting tip 20 can be initially enclosed or covered by a relatively soft sheath, referred to hereafter as tip 134, such as a soft polymeric material, e.g. rubber or silicone, to protect the cutting blades of the cutting member 126 and to prevent the inadvertent cutting of tissue while inserting the sound 12 through the urethra 16. Upon moving the cutting tip 20 axially outwardly from the sound 12, the cutting tip 20 can readily penetrate the relatively soft sheath to expose the cutting tip 20 for penetrating through the bladder 18 and out the abdomen wall 22.

Figure 19:
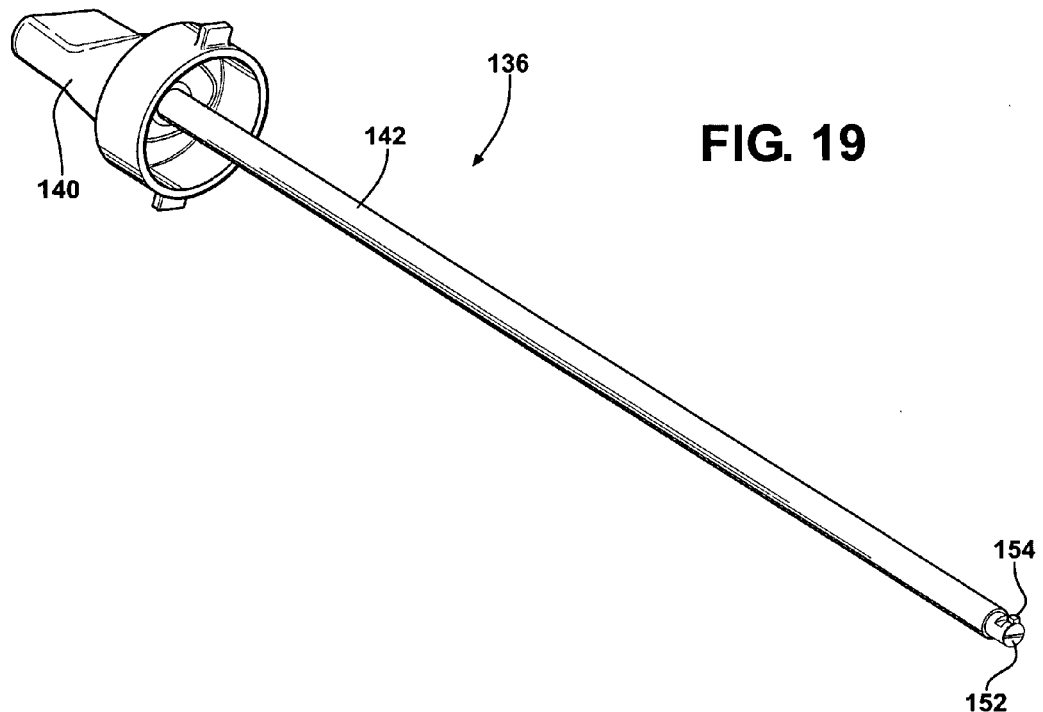
FIG. 19 is a perspective view of a stylet of the dilator assembly.
Figure 20:
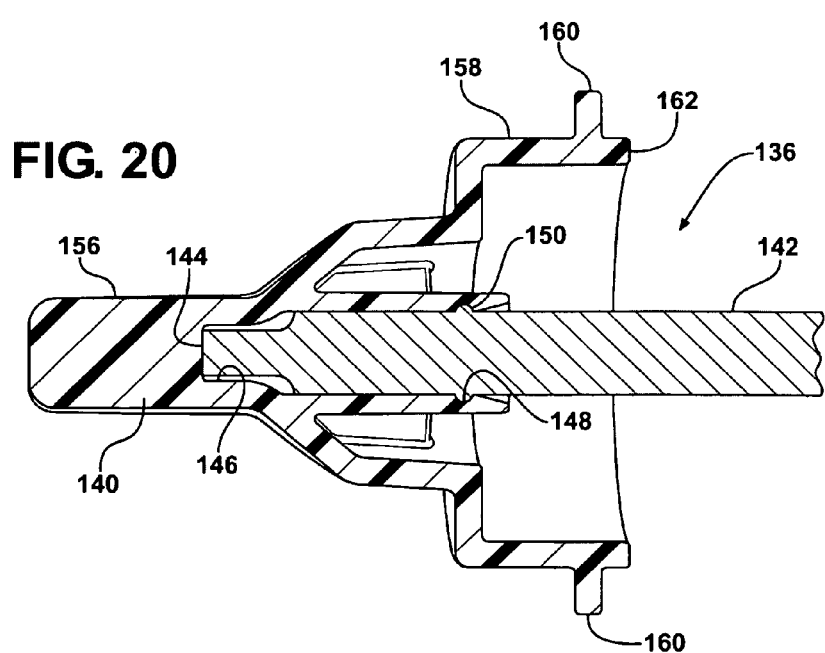
FIG. 20 is an enlarged partial cross-sectional view of the stylet of FIG. 19 showing a stylet handle attached to a stylet rod.

As shown in FIG. 14, the dilator assembly 11 includes a stylet 136 (FIG. 19) and a dilator housing assembly 138. The stylet 136 is represented here, by way of example and without limitation, as having a two piece construction, including a stylet rod handle, referred to hereafter as handle 140, and a stylet rod, referred to hereafter as rod 142. The handle 140 and rod 142 can be constructed of any suitable, rigid plastic, metal or material composition. For example, the handle 140 can be molded from a plastic material, while the rod 142 can be constructed from a polycarbonate material. Upon being attached to one another, the handle 140 and rod 142 are prevented from relative rotation. To facilitate preventing relative rotation, one end 144 of the rod can have a non-circular configuration in lateral cross-section, such as a rectangular shape, for example, while the handle 140 can be provided with a pocket 146 having substantially the same shape in cross-section, thereby providing a tight press fit or line-to-line fit between the end 144 and the pocket 146. To prevent relative axial movement between the handle 140 and the rod 142, a snap fit can be provided between the handle 140 and rod 142. The snap fit can be provided via snapping interaction between an annular recess 148 in one of the pocket 146 or rod 142, shown here as being in the pocket 146, for example, and an annular rib 150 in the other of the pocket 146 or rod 142, shown here as being on the rod 142, for example.

The rod 142 has a straight body that extends from the handle 140 to a free end 152. The free end 152 is configured for operable attachment to the sound 12 via the connector 71 on the advancement member 68. The free end 152 has a bayonet-type connector 154 configured the same as the connector 128 on the cutting tip 20. Accordingly, the free end 152 can be attached to the advancement member 68 through relative rotation between the connector 71 and the connector 154, and detached from the advancement member 68 through relative rotation between the connector 71 and the connector 154. It should be recognized that other mechanisms that accomplish selective, releasable attachment between the free end 152 of the rod 142 and the end 70 of the advancement member 68 are contemplated to be within the scope of the invention.

The handle 140 has an upstanding gripping knob 156 with an annular base 158 of a predetermined diameter depending therefrom. The gripping knob 156 can be configured as desired to facilitate the surgeon's ability to grip, rotate and pull the handle 140. The gripping knob 156 is illustrated here, by way of example and without limitation, as having a generally rectangular wall with opposite sides suitable for gripping between a thumb and forefinger. The base 158 is configured for releasable attachment to the dilator housing assembly 138, thereby allowing the stylet 136 and the dilator housing assembly 138 to be maintained in locked relation with one another, until it becomes desired to remove the stylet 136 from the dilator housing assembly 138, such as at a selected time during the surgical procedure. To facilitate the releasable locking, the base 158 is represented here as having a pair of locking tabs 160 that extend radially outwardly from an outer surface of the annular base 158, with the locking tabs 160 being oriented diametrically opposite one another. The locking tabs 160 are spaced a predetermined distance from a flat bottom surface 162 of the annular base 158, thereby assuring proper locking interaction with the dilator housing assembly 138.

The dilator housing assembly 138 has a dilator housing 164, a pair of dilator arm assemblies 166, 168, and an expandable sheath 170. The dilator housing 164 has an frustroconical, annular body 172 extending between a first end 174 of one diameter and an opposite second end 176 of another diameter reduced from the first end 174. A pair of handles 178 extend radially outwardly from the first end 174 diametrically away from one another. The handles facilitate manipulating the dilator housing assembly 138 in use, and can be formed other than as shown, if desired. The body 172 has a pair of straight, elongate through slots 180 extending lengthwise between the first and second ends 174, 176. The slots 180 are arranged diametrically opposite one another, and are oriented between the handles 178.

As best shown in FIGS. 15 and 16, the dilator housing 164 has a generally cylindrical though passage 182 extending between the first and second ends 174, 176. A stop surface is located radially outwardly from the through passage 182, with the stop surface being represented here as an annular rib 184. The stop surface 184 is located adjacent the first end 174 to regulate insertion of the stylet 136 through the dilator housing 164 by abutting the locking tabs 160 on the handle 140 of the stylet 136. To facilitate fixing the stylet 136 relative to the dilator housing 164, the housing 164 has an end cover 186 constructed as a single piece of material with the handles 178, however as a separate piece of material from the body 172. The end cover 186 can be attached to the body 172 in a variety of ways, and is shown here as being attached using a snap-fit construction.

As shown in FIG. 16, the dilator housing 164, by way of example and without limitation, is constructed having a conical inner housing member 187 attached to a conical outer housing member 189, with the end cover 186 being snap-fit to the outer housing member 189. The inner housing member 187 has an annular ramped rib 188 spaced from an annular end flange 190 to provide a recessed annular groove 192 configured for snapping receipt of an annular, radially inwardly facing shoulder 191 of the outer housing member 189. The outer housing member 189 has a circumferentially extending slot 193 sized for snapping receipt of a radially inwardly extending tab 195 on the end cover 186. Accordingly, the dilator housing 164 and end cover 186 can be assembled via snap fits, and without the need for adhesives or other attachment mechanisms.

The end cover 186 has an end opening 194 of a predetermined diameter sized for close receipt of the annular base 158 of the stylet handle 140. Accordingly, the diameter of the annular base 158 is just slightly smaller than the diameter of the end opening 194 of the end cover 186. To provide the releasable locking of the stylet 136 to the dilator housing 164, a pair of notches 196 extend radially outwardly from the end opening 194, wherein the notches 196 are arranged diametrically opposite one another for close receipt of the locking tabs 160 therethrough. Accordingly, the notches 196 are just slight larger than the locking tabs 160. As shown in FIGS. 16 and 17, to provide positive stop surfaces for the locking tabs 160 while locking the stylet 136 to the dilator housing assembly 138, a pair of lips 198 depend from the end opening 194 over a predetermined portion of the opening 194 to present a pair of stop shoulders 200. The stop shoulders 200 are located to allow the stylet 136 to be rotated a predetermined number of degrees prior to engagement with the locking tabs 160, wherein the stop shoulders 200 are illustrated here as allowing the stylet 136 to be rotated about 90 degrees prior to reaching the fully locked position. A locking feature for the handle 140 is provided by an opposing bump profile (not shown) on the dilator housing assembly, of which, keep the tabs 160 and handle 140 from rotating out of position until such desired time to release the handle 140, at which time, the tabs 160 will slide over the opposing bumps upon counter-clockwise rotation of the handle 160. Of course, to unlock the stylet 136, the handle is simply rotated in an opposite counter-clockwise direction until the locking tabs 160 register with the notches 196, whereupon the stylet 136 can be pulled straight outwardly from the dilator housing 164.

As shown in FIG. 16, the sheath 170 is attached to the second end 176 of the dilator housing 164 with the sheath 170 being in coaxial alignment with the through passage 182 of the dilator housing 164. The sheath 170 is represented here as being attached by a press fit between an outer surface of an annular ring 202 and an inner surface of the dilator housing 164. Aside from being compressed by a tight fit, an adhesive and/or weld joint can be used to facilitate maintaining the sheath in fixed attachment to the dilator housing 164.

The sheath 170 has an expanded diameter end 204 captured between the annular ring 202 and the dilator housing 164 and a reduced diameter, cylindrical portion 206 extending between the dilator arm assemblies 166, 168. As such, a conical portion 208 extends between the expanded diameter end 204 and the reduced diameter portion 206. The reduced diameter portion 206 is expandable, thereby being able to receive the enlarged diameter obturator-cannula assembly 13 therethrough. As best shown in FIG. 16A, the expanding capacity of the reduced diameter portion 206 is preferably provided by a polymeric material having reverse folded regions, referred to hereafter as pleats 210, extending along the axial length of the sheath 170. The reverse folded pleats 210 are formed having a generally z-shape in lateral cross-section, and can be maintained in a folded configuration by a RF tack welds and/or an adhesive, if desired. Regardless of the mechanism used to maintain the reverse folder regions in their "as folded" configuration, as best shown in FIG. 31A, the disposal of the oburator-cannula assembly 13 through the sheath 170 causes the reverse folded pleats 210 to readily unfold, thereby allowing the sheath 170 to attain its maximum diameter. Preferably, the maximum diameter of the sheath 170 is selected to be line-to-line with or slightly larger than the diameter of the oburator-cannula assembly 13. Accordingly, the forced required to push the oburator-cannula assembly 13 through the sheath 170 is that required to expand or unfold the reverse folded regions, which, if tack welded or adhered, is largely determined by the force required to break the weld joints and/or to break the adhesive joints, which is believed to be less than the force required to expand an elastic covered mesh fabric.

The dilator arm assemblies 166, 168 each have a dilator arm 212. The dilator arms 212 are constructed of a resilient, rigid polymeric material, such as polycarbonate, in an extrusion process, for example. As best shown in FIG. 16, each dilator arm 212 is formed as a hollow, generally flat, tubular member, having a tubular wall providing a hollow channel 214 extending from one end 216 that is attached to the dilator housing 164, with the channel 214 being aligned with and open to the slots 180, to an opposite end 218 (FIG. 15) extended away from the dilator housing 164. The ends 218 are each closed off by C-shaped retainer clips, referred to hereafter as fingers 220, 222. The fingers 220, 222 are shaped the same, however, the fingers 220, 222 are offset axially with one another to avoid interfering with one another. As such a C-shaped opening 224 formed by the axially outermost C-shaped finger 220 is able to freely register axially with a C-shaped opening 226 formed by the axially innermost C-shaped finger 220.

Each of the dilator arms 212 has an elongated opening, referred to hereafter as window 228, in a radially outward facing surface immediately adjacent the respective finger 220, 222. As such, the windows 228 face diametrically away from one another in mirrored relation to one another. The windows 228 have a predetermined width and length to allow respective dilation tab portions, referred to hereafter as dilation tabs 230, slidably received in the hollow channels 214 to be deployed outwardly from the windows 228, discussed further below.

As shown in FIG. 16, the dilation tabs 230 are constructed as elongate strips of resilient polymeric material that extend the full length of the channels 214 in the dilation arms 212. The tabs 230 have one end 232 that abut the respective finger 220, 222 and an opposite end 234 that extends axially outwardly beyond the ends 216 of the dilation arms 212. The ends 234 are operably attached to gripping dilator deployment members, referred to hereafter as gripping members or buttons 235, and are shown here, by way of example and without limitation, as being formed as one piece of material therewith, to facilitate actuating and de-actuating the dilation tabs 230. The buttons 235 are received and maintained outwardly of the dilator housing 164 for sliding movement along an outer surface of the slots 180. The dilation tabs 230 are constructed having a length corresponding to the distance extending between the respective fingers 220, 222 and the far end of the slots 180 adjacent the end cover 186.

As shown in FIG. 22, the obturator-cannula assembly 13 includes an elongate tubular member, referred to hereafter as a cannula 236 and an elongate rod member, referred to hereafter as an obturator 238. The cannula 236 has a tubular, cylindrical body 240 extending from a free end 242 to an opposite end 244 that is attached to an enlarged diameter cylindrical housing 246. The body 240 preferably extends over a length sufficient to extend slightly beyond the fingers 220, 222 of the dilator arms 212 during use. The body 240 can be constructed with a through passage 241 having a range of inner diameters to provided the desired size through passage into the bladder 18, such as an inner diameter corresponding to between about 15 to 40 French, for example. The tubular body 240 has a wall that is sufficiently rigid to resist bending or collapse, while remaining sufficiently thin to avoid being bulky, such as between about ¼-1 mm, for example. The housing 246 has a generally flat base 248 configured for flush abutment with the end cover 186 during use, whereupon, as mentioned, the free end 242 of the tubular body 240 extends slight beyond the fingers 220, 222. The housing 246 has an inner cavity 250 enlarged from the tubular through passage, with a plurality of ribs 252 extending radially inwardly from an inner wall surface 254 of the housing 246 to act as a stop surface for the obturator 238 during use. The ribs 252 are represented as extending from a base of the cavity 250 to a generally flush relation with an end 256 of the housing.

The housing 246 has a cover 258 attached adjacent the end 256. The cover 258 is operable to be pivoted between open and closed positions to allow direct access to the through passage of the cannula 236 and to close of the through passage of the cannula 236, respectively. The cover 258 is represented here as being attached to the housing 246 via a living hinge 260, although other hinge configurations are contemplated herein. Upon closing the cover 258, a tight seal is established between the cover 258 and the housing 246, wherein seals could be incorporated, such as o-ring seals (not shown), for example, could be incorporated between the housing 246 and the cover 258.

To allow an instrument to pass through the cover 258 while in its closed and sealed position, the cover 258 can be provided with an upper sealing surface 264 constructed of a resilient polymeric membrane or wall, such as from silicone, for example, with a slit or plurality of slits 266. The slits 266 are represented here as being in an X-shaped pattern, such that the instrument can be readily disposed through the center of the X-shaped pattern and into the through passage of the cannula 236. Upon withdrawing the surgical instrument from the cover 258, the resilient sealing surface retains its sealing capacity to prevent unwanted matter from entering the cannula 236 and/or to prevent fluids, such as saline or urine from the bladder, from exiting.

The obturator 238 has an elongate, straight cylindrical body 268 extending between a tapered, conical free end 270 and an enlarged diameter push knob 272. The cylindrical body 268 is preferably provided having an outer diameter slightly less than the inner diameter of the cannula 236 such that the obturator 238 is free to slide within the cannula 236. The cylindrical body 268 is provided as a generally rigid member having a length such that upon being fully inserted through the cannula 236, the enlarged push knob 272 abuts the ribs 252 in the housing 246, with the ribs 252 acting as a positive stop, and the conical free end 270 extends outwardly from the free end 242 of the cannula 236 to provide a substantially smooth transition between the body 240 of the cannula 236 and the body 268 of the obturator 238.

As shown in FIG. 8, the inside-out suprapubic transurethral procedure is initiated by inserting the distal portion 30 of the sound 12 through the urethra 16 and into the bladder 18. During insertion of the sound 12 through the urethra 16, the cutting tip 20 is covered with the tip 134 to prevent inadvertent damage from occurring to the urethra 16. The mast 42 can be inserted and locked in the mount sleeve 40 and the alignment guide arm 14, with the capture cup 96 attached to the housing 106, can be slid onto the mast 42 and temporarily locked in the desired position via the mast locking mechanism 48. The tip or free end of the distal portion 30 is positioned against the inside surface of the bladder 18, generally about 1-2 finger widths above a pubic bone 152, to establish a slight "tenting" of the bladder 18 and abdominal wall 22, as shown in FIG. 9. The tenting facilitates moving the bowel away from the distal portion 30 of the sound 12, and thus, away from the cutting tip 20. With the exception of obese to morbidly obese patients, the tenting is generally observable externally by the surgeon.

Next, as shown in FIG. 10, the alignment guide arm 14 can be released from the locked position on the mast 42 and lowered into compressing engagement with the outer skin surface of the abdominal wall 22. With the housing 106 of the alignment guide arm 14 properly positioned against the abdomen wall 22, the mast locking mechanism 48 can again be locked, thereby maintaining the apparatus 10 in the desired position.

Figure 11:
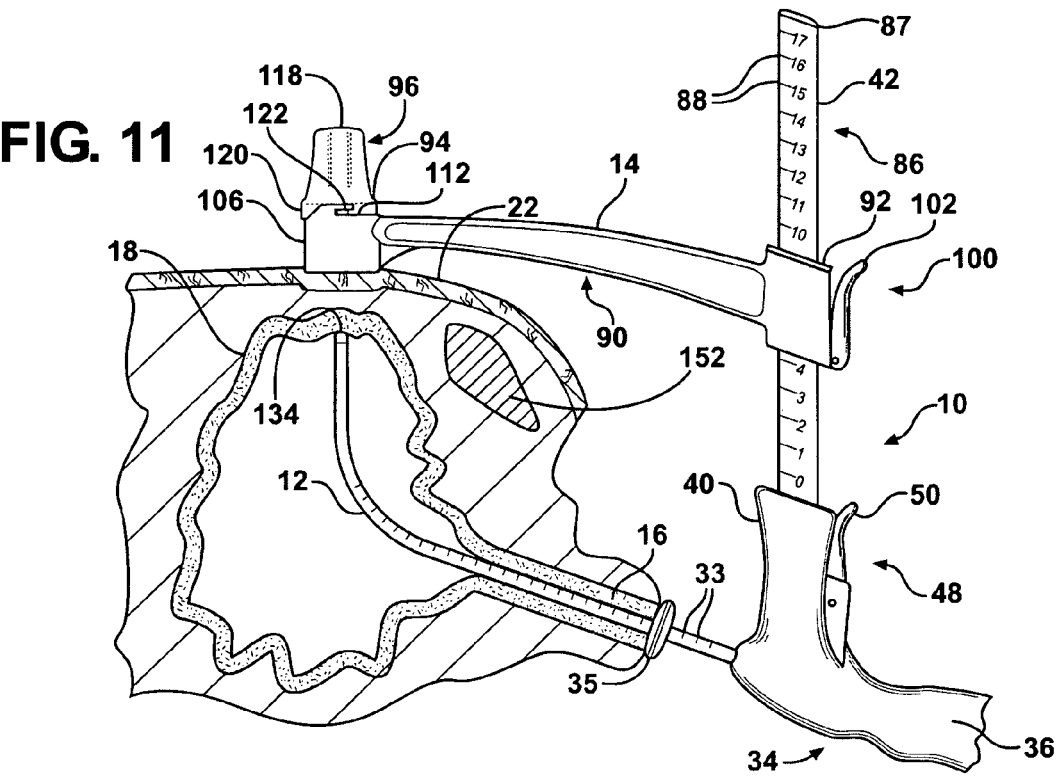
FIG. 11 is a side view showing a penetration depth marker of the apparatus moved adjacent an opening of the urethra.

Then, as shown in FIG. 11, upon locking the alignment guide arm 14 in the desired location over the abdomen wall 22, the penetration depth marker 35 can be moved forward to the opening of the urethra 16 to prevent further movement of the sound 12. The measurement or indicator markings 33 can be observed by the physician.

Figure 12:
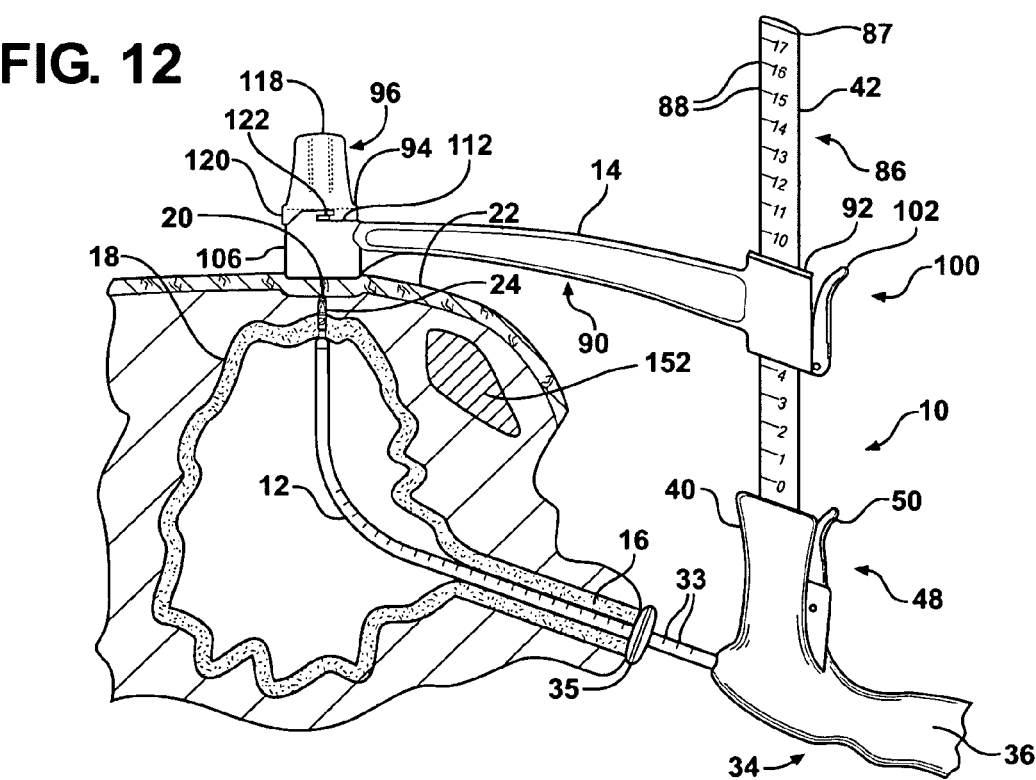
FIG. 12 is a side view showing the cutting tip penetrating the bladder and abdominal wall.

Next, as shown in FIG. 12, the cutting tip 20 can be advanced to penetrate through the protective tip 134, through the bladder 18 and through the abdominal wall 22. This is performed by rotating the wheel 58 of the cutting tip locking mechanism 56 from the locked position to the unlocked position, thereby biasing the brake spring 62 out of engagement with the respective notch 76 in the advancement member 68. Accordingly, the advancement member 68 is free to slide within the tubular body 36 and the sound 12 upon pushing on the rear handle 74. As the rear handle 74 is pushed, the surgeon is able to visually see from the scaled markings 67 on the tubular body 36 how far the advancement member 68, and thus, the cutting tip 20, is being advanced. In addition, the surgeon can readily determine an indication of the distance from the inside of the bladder wall 18 to the outside of the abdomen wall 22 via the measured markings 88 on the mast, and thus, the surgeon knows generally how far the cutting tip 20 must be advanced to penetrate the abdomen wall 22. While being advanced outwardly from the tip 134 and away from the sound 12, the advancement member 68 remains rigid along the length extended away from the sound 12 to allow it to penetrate the abdomen wall 22 in a controlled and substantially straight path such that it remains in constant coaxial alignment with the housing 106 of the alignment guide arm 14 and the capture cup 96.

Figure 13:
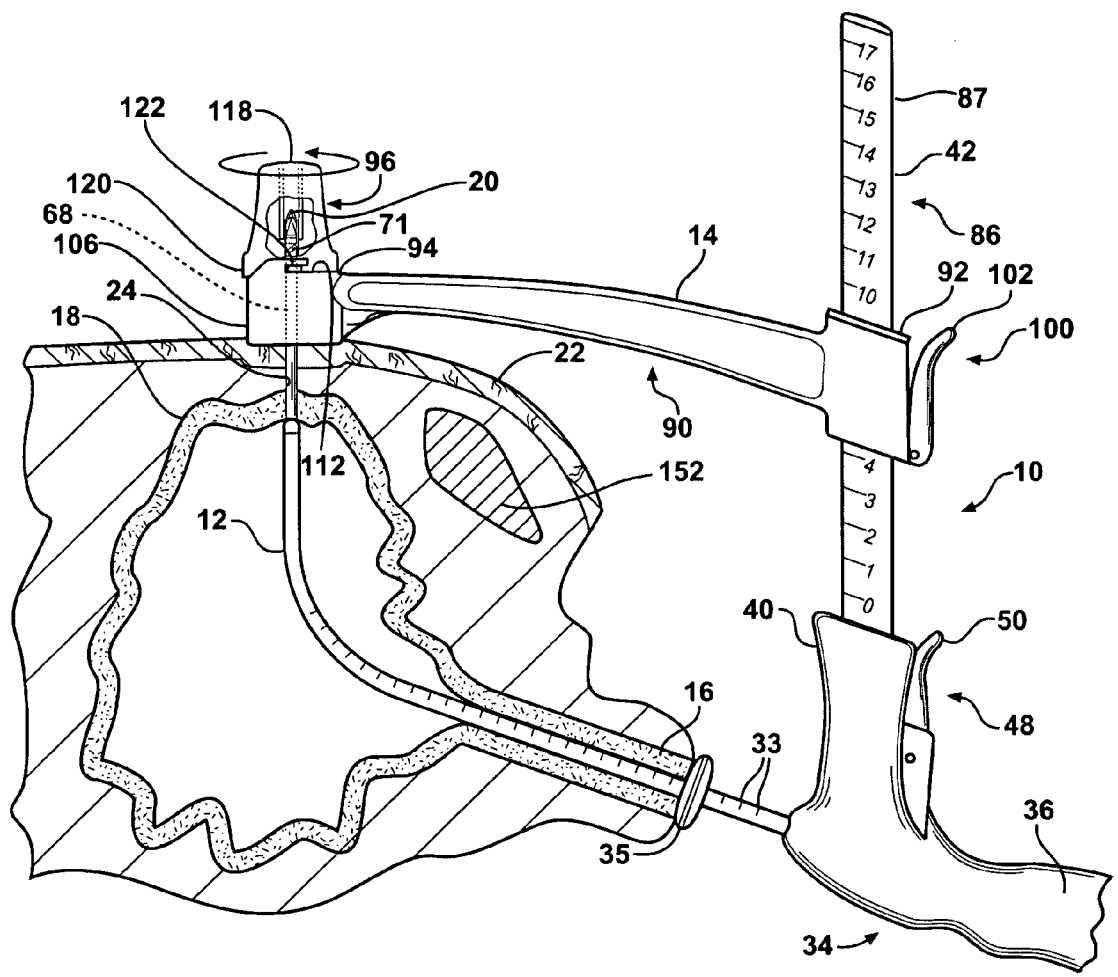
FIG. 13 is a broken away side view showing the cutting tip fully penetrated through the bladder and abdominal wall and received in the capture cup.

As shown in FIGS. 13 and 13A, the cutting tip 20 is then advanced into and captured in the capture cup 96 of the alignment guide arm 14, whereupon the cutting tip 20 can be released and disposed in a hands-free procedure.

Figure 23:
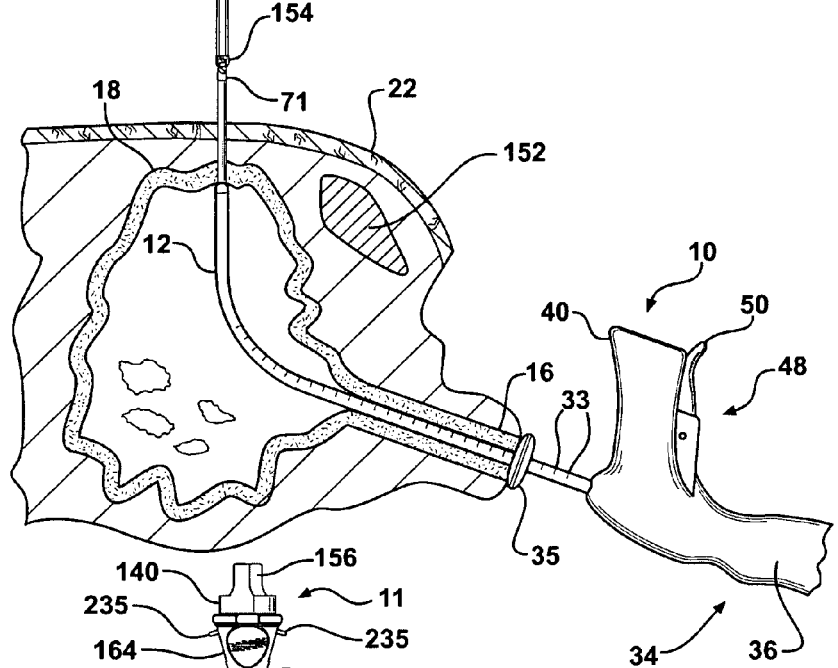
FIG. 23 is a side view showing an end of the stylet rod of the dilator assembly attached to the collet of the advancement member external to the abdominal wall.

As shown in FIG. 23, with the connector 71 on the advancement member 68 exposed outwardly from the abdominal wall 22, the connector 154 on the rod 142 of the dilator housing assembly 138 can be attached thereto. While in this position, the stylet 136 is preferably locked to the dilator housing assembly 138.

Figure 24:
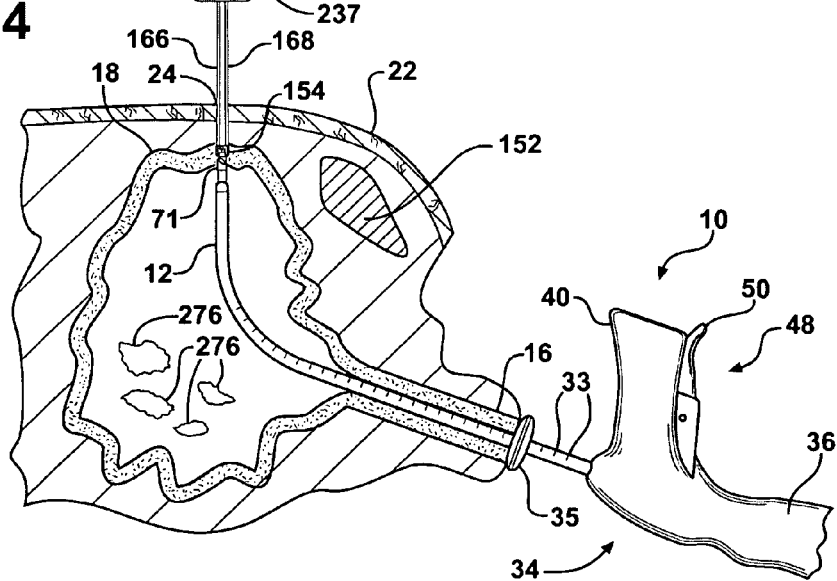
FIG. 24 is a view similar to FIG. 23 showing the end of the stylet rod and the dilator assembly being pulled through the abdominal wall and into the bladder.

As shown in FIG. 24, upon attaching the dilator assembly 11 operably to the sound 12 via the advancement member 68, the procedure continues by pulling or drawing the advancement member 68 back through the opening 24 and into the bladder 18. Accordingly, the free end 152 of the rod 142, along with the free ends of the dilator assemblies 166, 168 and the free end of the sheath 170, are drawn into the bladder 18.

As shown in FIG. 25, with the dilator arm assemblies 166, 168 having been drawn sufficiently into the bladder 18, the buttons 235 of the dilator arms 212 are slid along the outer surface of the housing body 164 from adjacent the first end 174 of the body 164 toward the second end 176 of the body 164. The buttons 235 are locked in place by a pair of opposing bump profiles extended inward from the side walls of the slots 180, which interface with an opposing profile surface on the lower section of the buttons 235 (not shown) offering a small resistance that is overcome when the buttons 235 snap in place, and therefore, releasably locked in place. This keeps the dilation tabs 230 from re-deploying back through the windows 228 of the dilation arms 212. As such, the dilation tabs 230 are caused to be compressed, with the ends 232 of the dilation tabs 230 abutting the respective fingers 220, 222, thereby causing portions of the dilation tabs 230 beneath and proximate the windows 228 to extend outwardly from the windows 228. The portions are bowed in a radially outwardly V-shaped configuration radially outwardly from the windows 228, thereby presenting a barrier to entry of the dilator arms 212 back into the surgically formed opening 24. Accordingly, the generally V-shaped portions of the dilation tabs 230 act to maintain the dilator arms 212 in the bladder and to prevent the dilator arms 212 from being pulled outwardly from the opening 24.

Figure 27:
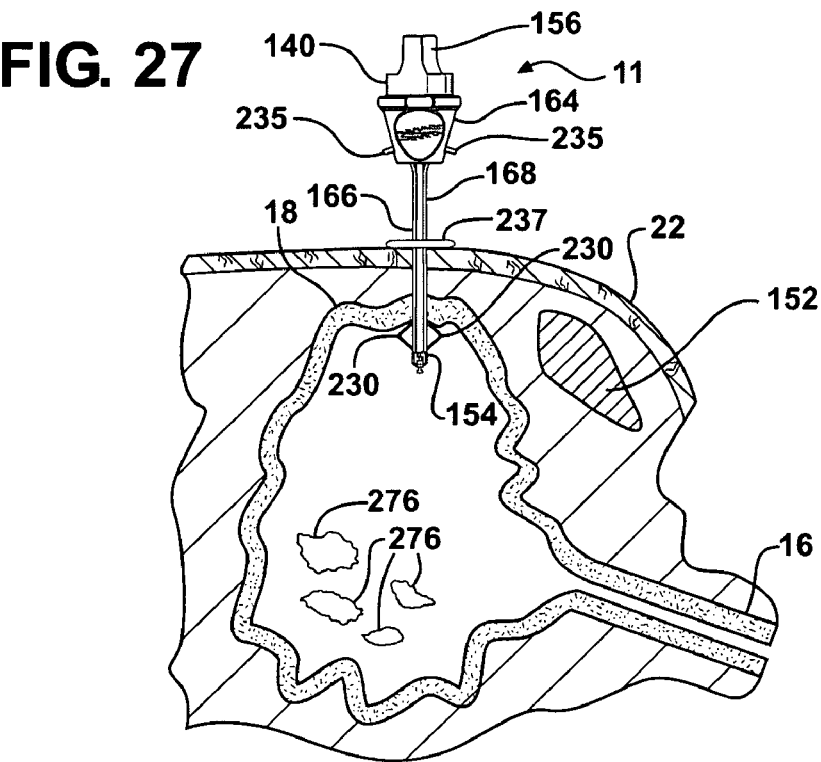
FIG. 27 is a side view showing the transurethral suprapubic cystostomy apparatus disconnected from the dilator assembly and removed from the patient.

Then, with the dilation tabs 230 expanded, the procedure continues by uncoupling or detaching the dilator assembly 11 from the advancement member 68. With the advancement member 68 maintained in a stationary position relative to dilator assembly 11, the stylet 136 is rotated relative to the stationary advancement member 68 by twisting the gripping knob 156 on the handle 140 of the stylet 136 in a counter-clockwise direction. The relative rotation between the connector 154 of the stylet 136 and the connector 71 of the advancement member 68 causes the two connectors 154, 71 to become disconnected, while in the bladder 18, thereby allowing the advancement member 68 to be pulled away from the stylet 136, wherein the procedure continues by withdrawing the advancement member 68 from the urethra 16 in combination with the sound 12, as shown in FIG. 27.

Figure 28:
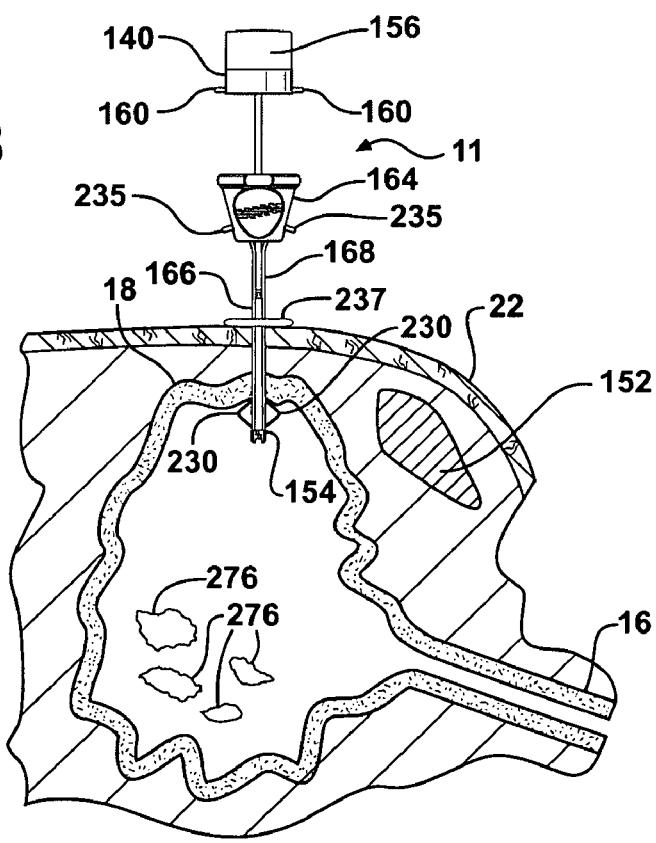
FIG. 28 is a view similar to FIG. 27 showing the stylet being removed from a sheath of the dilator assembly.
Figure 29:
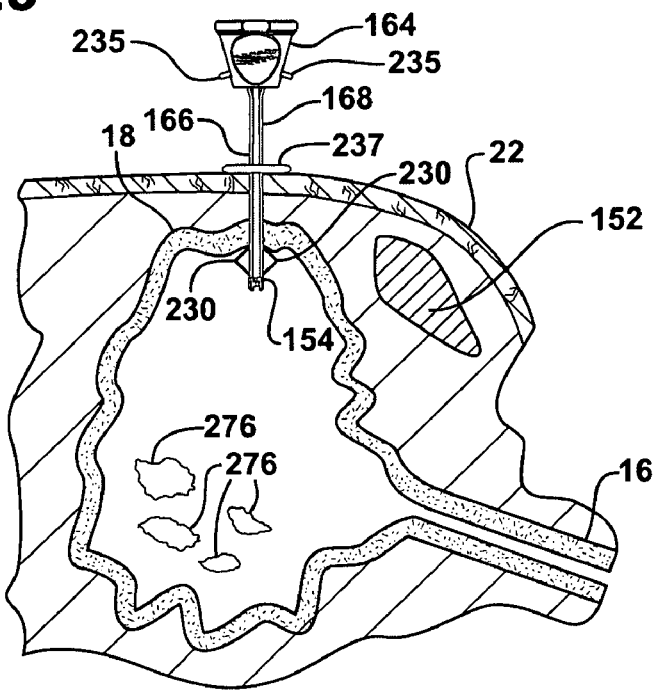
FIG. 29 is a view similar to FIG. 28 showing the stylet removed from sheath.

As shown in FIGS. 28 and 29, with the advancement member 68 disconnected from the stylet 136, the procedure continues by removing the stylet 136 from the dilator assembly 11 with the dilator arm assemblies 166, 168 and sheath 170 remaining in place, at least partially received in the bladder 18. The stylet 136 can be pulled axially from the dilator housing assembly 138 by rotating the handle 140 until the locking tabs 160 are registered with the slots 196.

Figure 30:
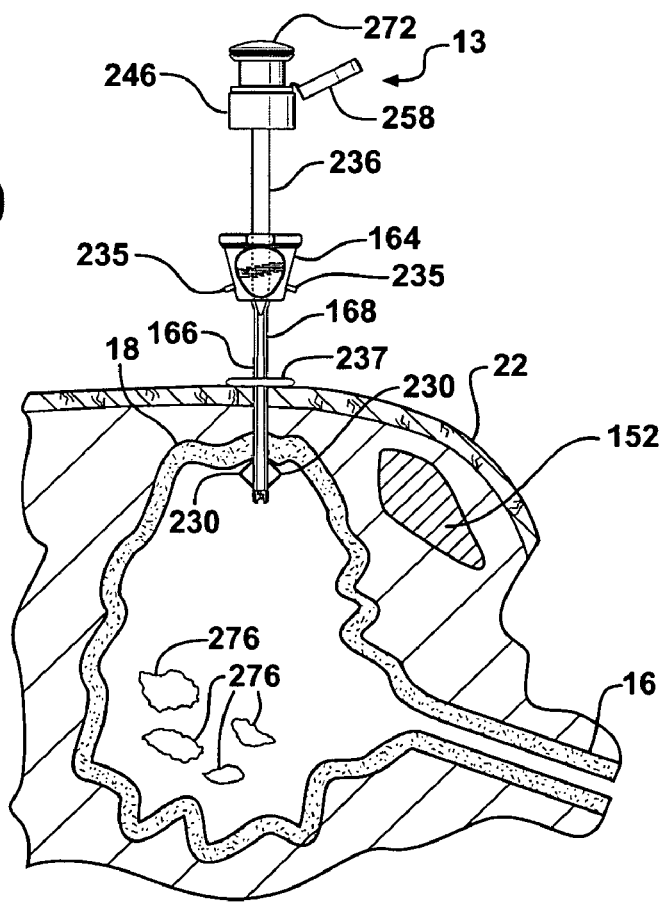
FIG. 30 is a side view showing the obturator-cannula assembly being disposed into the sheath of the dilator assembly.
Figure 31:
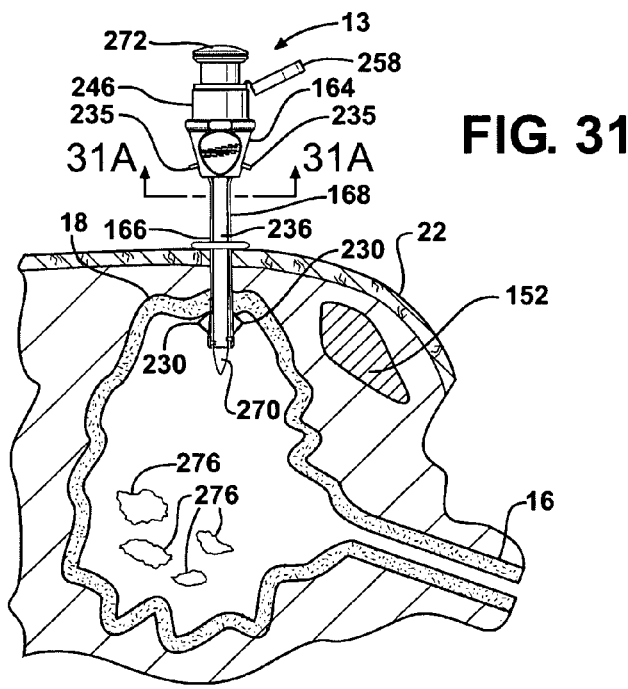
FIG. 31 is a view similar to FIG. 30 showing the obturator-cannula assembly disposed fully through the sheath.
Figure 31A:
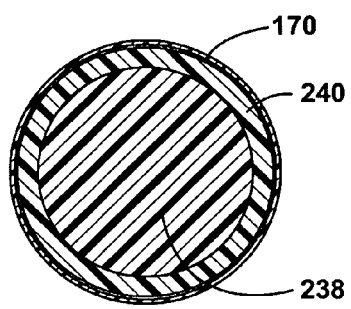
FIG. 31A is a cross-sectional view taken generally along the line 31A-31A of FIG. 31.
Figure 32:
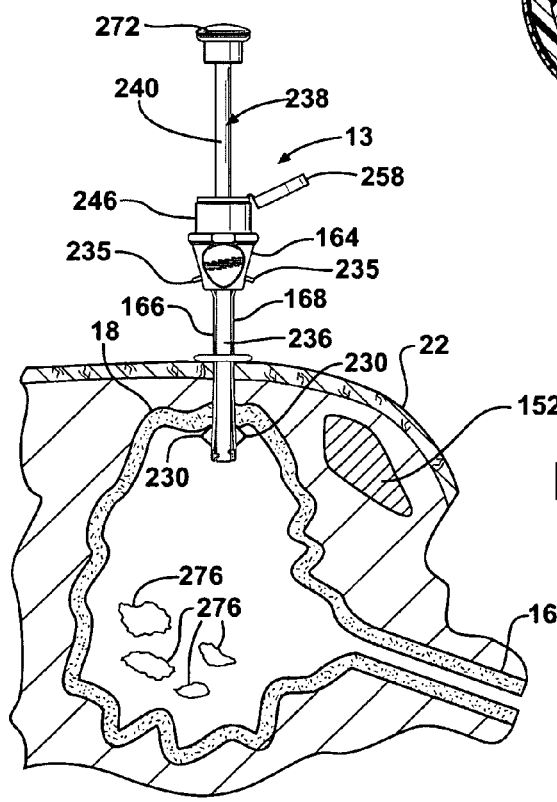
FIG. 32 is a view similar to FIG. 31 showing the obturator being removed from the cannula with the cannula remaining disposed in the sheath.
Figure 33:
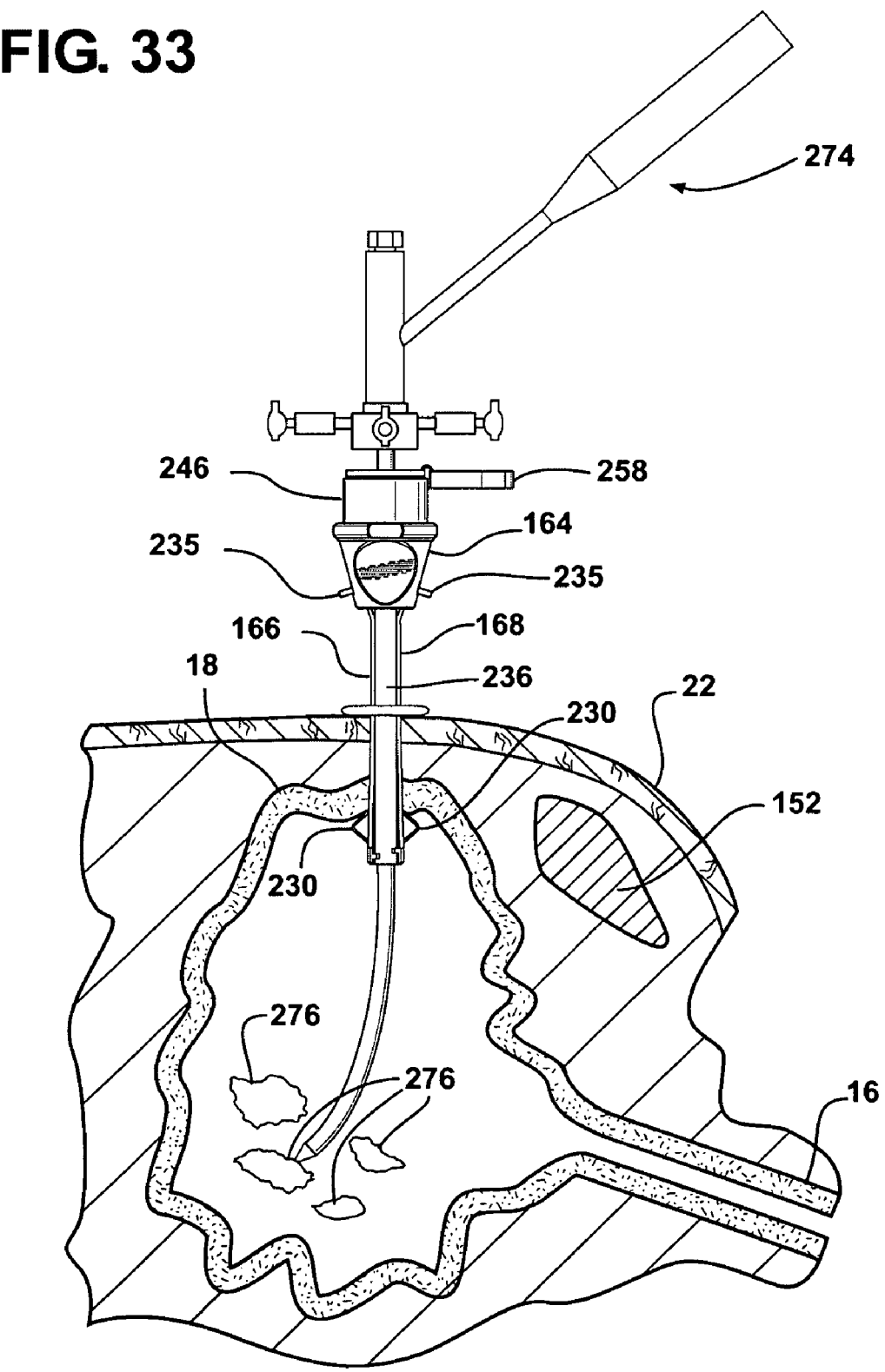
FIG. 33 is a view showing a surgical instrument disposed through the cannula and into the bladder.

Then, as shown in FIGS. 30 and 31, the procedure continues by inserting the obturator-cannula assembly 13 through the sheath 170 of the dilator housing assembly 138 by applying an axially directed force on the push knob 272. The obturator-cannula assembly 13 is inserted axially through the sheath 170 until the push knob 272 abuts the ribs 184 on the housing body 172. While inserting the obturator-cannula assembly 13 through the sheath 170, the dilator arms 212 are biased outwardly due to the enlarged diameter of the assembly 13, wherein the conical free end 270 facilitates deflection of the dilator arms 212. Upon being fully inserted, the conical free end 270 of the obturator body 268 and the free end 242 of the cannula 236 are preferably extended axially beyond the fingers 220, 222 of the dilator arms 212 into the bladder 18. Further, the free end 242 of the cannula 236 is substantially flush with the end of the sheath 170. In addition, with the cannula 236 fully inserted, the sheath 170 is caused to expand from its reduced first diameter to its enlarged second diameter via the pleats 210 being unfolded from their reverse folded construction. Then, as shown in FIG. 32, the obturator 238 is removed outwardly from the cannula 236, thereby leaving the through passage 241 unobstructed for easy access to the inside of the bladder 18. To prevent foreign matter from entering the through passage 241, the cover 258 can be closed on the housing 246. With the cover 258 having the slits 266, an instrument 274 can be extending in sealed relation through the slits 266, through the through passage 241 and into the bladder 18, such as those used to ablate bladder calculi 276, for example. Otherwise, the cover 258 can remain open, as shown in FIG. 32, while inserting an instrument into the bladder 18.

Obviously, many modifications and variations of the present invention are possible in light of the above teachings. It is, therefore, to be understood that within the scope of the appended claims, the invention may be practiced otherwise than as specifically described.

What is claimed is:

1. A bladder access apparatus, comprising a dilator, a cannula and an obturator in combination, for insertion into and expansion of and access through a surgical opening between an exterior abdominal wall and a bladder;

said dilator comprising:

an annular body having opposite first and second ends with a through passage extending between the ends, the annular body having a pair of slots opposite one another and extending lengthwise inbetween the first and second ends;

an elongated stylet connectable to the first end of the annular body, the stylet having a rod extending longitudinally through the through passage to a rod end located beyond the second end of the annular body when the stylet is connected to the first end of the annular body, the stylet disconnectable from the annular body to remove and withdraw the rod from within the through passage;

a pair of elongated arms connected to the second end of the annular body and extending longitudinally on opposite sides of the through passage and on opposite sides of and along the rod when the stylet is connected to the annular body, each arm extending from the second end of the annular body to a free end which is longitudinally spaced from the second end of the annular body at a location adjacent to the rod end, each arm comprising a tubular member having a hollow channel aligned with a separate one of the slots in the annular body, each tubular member having a window extending from the channel through the tubular member at a position adjacent to each free end, each window facing away from the rod in the tubular member in which the window is located;

an elongated resilient strip slidably received in each channel, a first end of each strip having a gripping member attached thereto which extends outward through the aligned slot in the annular body and which moves along the slot between locked and unlocked positions, a second opposite end of each strip located in the channel at the window, an extension portion of the second end of each strip extending outward from the window beyond the tubular member upon moving the gripping member to the locked position, and the extension portion retracting into the window and the channel upon moving the gripping member to the unlocked position; and an arm connector which connects the free end of each arm to the rod end when the stylet is connected to the annular body, the arm connector releasing the free ends of each arm from the rod end upon disconnection of the stylet from the annular body and removal of the rod from the through passage;

said cannula comprising:

a rigid elongated hollow tubular body adapted to be inserted within the through passage of the annular body and to extend between the arms after disconnection of the stylet from the annular body and removal of the rod from within the through passage, the hollow tubular body defining an interior passage extending between opposite ends of the tubular body; and said obturator comprising:

a rigid cylindrical member sized for receipt within the interior passage of the tubular body and moveable with the tubular body upon insertion of the cylindrical member and tubular body within the through passage of the annular body after disconnection of the stylet from the annular body and withdrawal of the rod from within the through passage, the cylindrical member removeable from the interior passage of the tubular body after movement of the tubular body and the cylindrical member through the through passage of the annular body, the cylindrical member having a tapered free end which extends beyond the tubular body upon receipt within the interior passage of the tubular body; and wherein:

the free ends of the arms are positioned relatively close together when connected by the arm connector to the rod end;

the insertion of the cylindrical member within the tubular body through the through passage after disconnection and removal of the stylet causing the tapered free end of the cylindrical member to contact the arms and deflect the arms outward and expand the surgical opening with the arms are positioned relatively farther apart;

the removal of the cylindrical member from within the interior passage of the tubular body after expansion of the surgical opening by insertion of the cylindrical member within the tubular body through the through passage of the annular body and between the arms permitting access to the bladder through the interior passage of the tubular body; and the extension portion of each strip is extendable outward from the window while the arms are positioned relatively close together and when the arms have been deflected outward to hold the dilator within the surgical opening.

2. An apparatus as defined in claim 1, wherein said dilator further comprises:

an expandable tubular sheath having a first inside diameter and a second enlarged inside diameter upon expansion of the tubular sheath, the sheath attached to the annular body with the first and second inside diameters extending coaxially with the through passage and with the arms extending longitudinally along and exterior of the tubular sheath; and wherein:

the first inside diameter of the sheath permits receipt of the rod within the first inside diameter of the sheath;

the tubular body has a diameter greater than the first inside diameter of the sheath and less than the second inside diameter of the sheath; and the tapered end of the cylindrical member expands the sheath from the first inside diameter to the second inside diameter upon insertion of the cylindrical member and tubular body within a space defined by the first inside diameter previously occupied by the rod after removal of the rod from within the first inside diameter of the sheath and from the through passage of the annular body.

3. Apparatus as defined in claim 2, wherein the tubular body has an outer diameter substantially the same as the second inside diameter of the sheath.

4. Apparatus as defined in claim 3, wherein:
the sheath is formed substantially from an inelastic polymeric body.

5. Apparatus as defined in claim 4, wherein:
the sheath includes at least one reverse folded pleat extending substantially along its length when the sheath has the first inside diameter; and
the one pleat is substantially unfolded when the sheath expands into the second inside diameter.

6. Apparatus as defined in claim 2, wherein:
the rod has a length sufficient to position the rod end beyond the sheath when the stylet is connected to the annular body; and
the arm connector connects the free ends of each arm to the rod end beyond the sheath when the stylet is connected to the annular body.

7. Apparatus as defined in claim 1, wherein:
said dilator is inserted through the surgical opening with the use of a transurethral suprapubic instrument inserted through a urethra and into the bladder; and
the stylet includes a handle which is connectable to the first end of the annular body and an insertion connector at the rod end, the insertion connector adapted for attachment to the transurethral suprapubic instrument to move the dilator through the surgical opening with the free ends of the arms connected to the rod end until the free ends and the windows are located within the bladder.

8. Apparatus as defined in claim 7, wherein:
the insertion connector comprises a bayonet type connector.

9. Apparatus as defined in claim 7, wherein the transurethral suprapubic instrument comprises:
an elongated tubular instrument body having a distal portion adapted to be inserted through the urethra and into the bladder and a proximal portion adapted to remain outside of the urethra for manipulating the distal portion within the urethra and the bladder; and
an elongated advancement member moveably positioned within the instrument body, the advancement member having a connector portion adapted for releasable attachment to rod end.

10. Apparatus as defined in claim 7, wherein:
the first end of the annular body includes at least one slot; and
the handle includes at least one tab adapted for receipt in the slot to connect the stylet to the annular body.

11. Apparatus as defined in claim 1, wherein:
the arm connector includes a finger on each free end of each arm;
the fingers on the free ends of the arms face one another in an overlapping relationship relative to the rod end; and
each finger defines an opening within which to receive the rod end to hold the free end of each arm adjacent to the rod end when the stylet is connected to the annular body.

12. Apparatus as defined in claim 11, wherein:
the opening of each finger is c-shaped; and
the fingers are retained to the free end of the rod when the rod end is located within the c-shaped openings.

13. A method of providing access into the bladder through the abdominal wall using the apparatus defined in claim 1, comprising:

forming the surgical opening through the bladder and the abdominal wall;

inserting a distal end of a transurethral suprapubic instrument into the urethra while maintaining a proximal end of the transurethral suprapubic instrument outside of the urethra;

extending the distal end of a transurethral suprapubic instrument through the surgical opening and out of the abdominal wall;

attaching the rod end to the distal end of the transurethral suprapubic instrument;

moving the dilator through the surgical opening until the windows of the free ends of the arms are located within the bladder by withdrawing the distal end of the transurethral suprapubic instrument through the surgical opening into the bladder while the distal end of the transurethral suprapubic instrument is attached to the rod end;

moving the gripping members to the locked positions to extend the extension portion of each strip outward from each window within the bladder;

disconnecting the stylet from the annular body and removing the rod from within the through passage to disconnect the arm connector and release the free ends of the arms from the rod end within the bladder;

pushing the tubular body and cylindrical member through the through passage; and removing the cylindrical member from within the interior passage of the tubular body to gain access into the bladder through the interior passage of the tubular body.

14. A method of providing access into the bladder through the abdominal wall using the apparatus defined in claim 2, comprising:

forming the surgical opening through the bladder and the abdominal wall;

inserting a distal end of a transurethral suprapubic instrument into the urethra while maintaining a proximal end of the transurethral suprapubic instrument outside of the urethra;

extending the distal end of a transurethral suprapubic instrument through the surgical opening and out of the abdominal wall;

attaching the rod end to the distal end of the transurethral suprapubic instrument;

moving the dilator through the surgical opening until the windows of the free ends of the arms are located within the bladder by withdrawing the distal end of the transurethral suprapubic instrument through the surgical opening into the bladder while the distal end of the transurethral suprapubic instrument is attached to the rod end;

moving the gripping members to the locked positions to extend the extension portion of each strip outward from each window within the bladder;

disconnecting the stylet from the annular body and removing the rod from within the through passage and withdrawing the rod out of the sheath to disconnect the arm connector and release the free ends of the arms from the rod end within the bladder;

pushing the tubular body and cylindrical member through the through passage to expand the expandable sheath from the first inside diameter to the second inside diameter until a forward portion of the tubular body resides within the bladder while a rear portion of the tubular body resides outside of the abdomen; and removing the cylindrical member from the interior passage of the tubular body to gain access into the bladder through the interior passage of the tubular body.

15. A method of providing access into the bladder through the abdominal wall using the apparatus defined in claim 5, comprising:

forming the surgical opening through the bladder and the abdominal wall;

inserting a distal end of a transurethral suprapubic instrument into the urethra while maintaining a proximal end of the transurethral suprapubic instrument outside of the urethra;

extending the distal end of a transurethral suprapubic instrument through the surgical opening and out of the abdominal wall;

attaching the rod end to the distal end of the transurethral suprapubic instrument;

moving the dilator through the surgical opening until the windows of the free ends of the arms are located within the bladder by withdrawing the distal end of the transurethral suprapubic instrument through the surgical opening into the bladder while the distal end of the transurethral suprapubic instrument is attached to the rod end;

moving the gripping members to the locked positions to extend the extension portion of each strip outward from each window within the bladder;

disconnecting the stylet from the annular body and removing the rod from within the through passage by pulling the rod out of the sheath to disconnect the arm connector and release the free ends of the arms from the rod end within the bladder;

pushing the tubular body and cylindrical member through the through passage to unfold the folded pleat thereby expanding the expandable sheath from the first inside diameter to the second enlarged inside diameter; and removing the cylindrical member from within the interior passage of the tubular body to gain access into the bladder through the interior passage of the tubular body.

16. A method of providing access into the bladder through the abdominal wall using the apparatus defined in claim 9, comprising:

forming the surgical opening through the bladder and the abdominal wall;

inserting a distal end of a transurethral suprapubic instrument into the urethra while maintaining a proximal end of the transurethral suprapubic instrument outside of the urethra;

advancing a portion of the advancement member of the transurethral suprapubic instrument through the surgical opening and outward from the abdominal wall;

attaching the rod end to the connector portion of the advancement member while the stylet is connected to the inner body and while the arm connectors are connected to the rod end;

moving the dilator through the surgical opening until the windows of the free ends of the arms are located within the bladder by withdrawing the distal end of the transurethral suprapubic instrument through the surgical opening into the bladder while the distal end of the transurethral suprapubic instrument is attached to the rod end;

moving the gripping members to the locked positions to extend the extension portion of each strip outward from each window within the bladder;

disconnecting the rod end from the connector portion of the advancement member;

disconnecting the stylet from the annular body and removing the rod from within the through passage to disconnect the arm connector and release the free ends of the arms from the rod end within the bladder;

pushing the tubular body and cylindrical member through the through passage; and removing the cylindrical member from within the interior passage of the tubular body to gain access into the bladder through the interior passage of the tubular body.

* * * * *